United States Patent
McKiernan et al.

(10) Patent No.: US 7,905,872 B2
(45) Date of Patent: *Mar. 15, 2011

(54) ABSORBENT ARTICLES COMPRISING A SLOW RECOVERY STRETCH LAMINATE

(75) Inventors: Robin Lynn McKiernan, Mason, OH (US); Bryn Hird, Colerain Twp., OH (US); Edward Joseph Urankar, Mason, OH (US); Janet Neton, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 816 days.

This patent is subject to a terminal disclaimer.

(21) Appl. No.: 11/144,497

(22) Filed: Jun. 3, 2005

(65) Prior Publication Data

US 2005/0273071 A1 Dec. 8, 2005

Related U.S. Application Data

(60) Provisional application No. 60/577,037, filed on Jun. 4, 2004, provisional application No. 60/643,920, filed on Jan. 10, 2005.

(51) Int. Cl.
*A61F 13/15* (2006.01)
*A61F 13/20* (2006.01)

(52) U.S. Cl. .............. 604/385.21; 604/358; 604/386; 604/387; 604/388; 604/389; 604/385.01; 604/390; 604/391; 604/392; 604/393; 428/903; 428/364; 428/913; 428/221; 428/492; 525/97; 525/98; 525/99

(58) Field of Classification Search ............. 604/385.21, 604/385.01, 386, 387, 388, 389, 390, 391, 604/392, 393; 428/903, 364, 913, 221, 492; 525/97, 98, 99

See application file for complete search history.

(56) References Cited

U.S. PATENT DOCUMENTS

| | | | | |
|---|---|---|---|---|
| 3,086,242 | A | * | 4/1963 | Cook et al. |
| 3,139,468 | A | * | 6/1964 | Wheat |
| 3,370,630 | A | * | 2/1968 | Gordon et al. |
| 3,587,581 | A | * | 6/1971 | Jones, Sr. |
| 3,592,946 | A | * | 7/1971 | Griffith |

(Continued)

FOREIGN PATENT DOCUMENTS

CH 528285 2/1968

(Continued)

OTHER PUBLICATIONS

PCT Search Report, mailed Dec. 27, 2005, 3 pages.

(Continued)

*Primary Examiner* — Tatyana Zalukaeva
*Assistant Examiner* — Ginger T Chapman
(74) *Attorney, Agent, or Firm* — John G. Powell; Richard L. Alexander; Eric T. Addington

(57) ABSTRACT

An absorbent article may comprise a topsheet, a backsheet joined with the topsheet, an absorbent core interposed between the topsheet and backsheet; and one or more article elements selected from the group consisting of an anal cuff, an elasticized topsheet, a fastening system, a leg cuff, a waist elastic feature, a side panel, an ear, and combinations thereof. The article elements may comprise a slow recovery stretch laminate exhibiting an unload force at 37° C. of about 0.16 N/(g/m) or greater and a percent of initial strain after 15 seconds of recovery at 22° C. of about 10% or greater.

25 Claims, 7 Drawing Sheets

U.S. PATENT DOCUMENTS

| | | | |
|---|---|---|---|
| 3,601,923 A * | 8/1971 | Rosenberg | |
| 3,639,917 A * | 2/1972 | Althouse | |
| 3,819,401 A * | 6/1974 | Massengale et al. | |
| 3,848,594 A | 11/1974 | Buell | |
| 3,860,003 A | 1/1975 | Buell | |
| 3,911,173 A | 10/1975 | Sprague, Jr. | |
| 3,912,565 A * | 10/1975 | Koch et al. | |
| 3,929,135 A | 12/1975 | Thompson | |
| RE28,688 E | 1/1976 | Cook | |
| 4,116,842 A * | 9/1978 | Meier | |
| 4,122,134 A * | 10/1978 | Miki et al. | |
| 4,152,370 A * | 5/1979 | Moczygemba | |
| 4,169,336 A * | 10/1979 | Kuhn | |
| 4,248,981 A * | 2/1981 | Milkovich et al. | |
| 4,248,982 A * | 2/1981 | Bi et al. | |
| 4,248,984 A * | 2/1981 | Bi et al. | |
| 4,259,220 A * | 3/1981 | Bunnelle et al. | |
| 4,324,246 A | 4/1982 | Mullane et al. | |
| 4,337,771 A * | 7/1982 | Pieniak et al. | |
| 4,342,314 A | 8/1982 | Radel et al. | |
| 4,346,198 A * | 8/1982 | Doak et al. | |
| 4,381,781 A | 5/1983 | Sciaraffa et al. | |
| 4,412,087 A * | 10/1983 | Trepka | |
| 4,418,180 A * | 11/1983 | Heinz et al. | |
| 4,450,026 A | 5/1984 | Pieniak et al. | |
| 4,463,045 A | 7/1984 | Ahr et al. | |
| 4,515,595 A | 5/1985 | Kievit et al. | |
| 4,573,986 A | 3/1986 | Minetola et al. | |
| 4,603,155 A * | 7/1986 | Muramori et al. | |
| 4,609,191 A * | 9/1986 | Remme | |
| 4,609,518 A | 9/1986 | Curro et al. | |
| 4,610,678 A | 9/1986 | Weisman et al. | |
| 4,629,643 A | 12/1986 | Curro et al. | |
| 4,636,207 A | 1/1987 | Buell | |
| 4,662,875 A | 5/1987 | Hirotsu et al. | |
| 4,673,402 A | 6/1987 | Weisman et al. | |
| 4,681,580 A * | 7/1987 | Reising et al. | |
| 4,695,278 A | 9/1987 | Lawson | |
| 4,698,242 A * | 10/1987 | Salerno | |
| 4,699,622 A | 10/1987 | Toussant et al. | |
| 4,699,941 A * | 10/1987 | Salerno | |
| 4,704,115 A | 11/1987 | Buell | |
| 4,704,116 A * | 11/1987 | Enloe | |
| 4,704,434 A * | 11/1987 | Kitchen et al. | |
| 4,710,189 A | 12/1987 | Lash | |
| 4,719,261 A * | 1/1988 | Bunnelle et al. | |
| 4,720,415 A * | 1/1988 | Vander Wielen et al. | |
| 4,761,198 A * | 8/1988 | Salerno | |
| 4,785,996 A | 11/1988 | Ziecker et al. | |
| 4,795,454 A | 1/1989 | Dragoo | |
| 4,808,178 A | 2/1989 | Aziz et al. | |
| 4,816,025 A | 3/1989 | Foreman | |
| 4,816,094 A * | 3/1989 | Pomplun et al. | |
| 4,820,590 A * | 4/1989 | Hodgson, Jr. et al. | |
| 4,834,735 A | 5/1989 | Alemany et al. | |
| 4,842,666 A | 6/1989 | Werenicz | |
| 4,846,815 A | 7/1989 | Scripps | |
| 4,857,067 A | 8/1989 | Wood et al. | |
| 4,874,255 A * | 10/1989 | Ball et al. | |
| 4,888,231 A | 12/1989 | Angstadt | |
| 4,892,536 A | 1/1990 | Desmarais et al. | |
| 4,894,060 A | 1/1990 | Nestegard | |
| 4,900,317 A | 2/1990 | Buell | |
| 4,909,803 A | 3/1990 | Aziz et al. | |
| 4,938,753 A | 7/1990 | Van Gompel et al. | |
| 4,939,208 A * | 7/1990 | Lanza et al. | |
| 4,940,464 A | 7/1990 | Van Gompel et al. | |
| 4,946,527 A | 8/1990 | Battrell | |
| 4,963,140 A | 10/1990 | Robertson et al. | |
| 4,965,122 A | 10/1990 | Morman | |
| 4,968,312 A | 11/1990 | Khan | |
| 4,981,747 A | 1/1991 | Morman | |
| 4,987,194 A | 1/1991 | Maeda et al. | |
| 4,988,344 A | 1/1991 | Reising et al. | |
| 4,988,345 A | 1/1991 | Reising | |
| 4,990,147 A | 2/1991 | Freeland | |
| 5,006,394 A | 4/1991 | Baird | |
| 5,026,364 A | 6/1991 | Robertson | |
| 5,028,646 A | 7/1991 | Miller et al. | |
| 5,036,978 A | 8/1991 | Frank et al. | |
| 5,037,416 A | 8/1991 | Allen et al. | |
| 5,047,484 A | 9/1991 | Tung | |
| 5,049,591 A | 9/1991 | Hayashi et al. | |
| 5,050,742 A | 9/1991 | Muckenfuhs | |
| 5,054,619 A | 10/1991 | Muckenfuhs | |
| 5,062,840 A | 11/1991 | Holt et al. | |
| 5,085,654 A | 2/1992 | Buell | |
| 5,089,558 A | 2/1992 | Hall et al. | |
| 5,092,861 A | 3/1992 | Nomura et al. | |
| 5,093,384 A | 3/1992 | Hayashi et al. | |
| 5,098,776 A | 3/1992 | Kobayashi et al. | |
| 5,114,781 A | 5/1992 | Morman | |
| 5,116,662 A | 5/1992 | Morman | |
| 5,118,762 A | 6/1992 | Chin | |
| 5,135,786 A | 8/1992 | Hayashi et al. | |
| 5,137,537 A | 8/1992 | Herron et al. | |
| 5,139,832 A | 8/1992 | Hayashi et al. | |
| 5,145,935 A | 9/1992 | Hayashi | |
| 5,147,345 A | 9/1992 | Young et al. | |
| 5,149,741 A | 9/1992 | Alper et al. | |
| 5,151,092 A | 9/1992 | Buell et al. | |
| 5,156,793 A | 10/1992 | Buell et al. | |
| 5,156,911 A | 10/1992 | Stewart | |
| 5,167,897 A | 12/1992 | Weber et al. | |
| 5,171,236 A | 12/1992 | Dreier et al. | |
| 5,188,627 A | 2/1993 | Igaue et al. | |
| 5,189,110 A | 2/1993 | Ikematu et al. | |
| 5,192,301 A | 3/1993 | Kamiya et al. | |
| 5,221,274 A | 6/1993 | Buell et al. | |
| 5,226,992 A | 7/1993 | Morman | |
| 5,234,999 A | 8/1993 | Tung et al. | |
| 5,242,436 A | 9/1993 | Weil et al. | |
| 5,246,433 A | 9/1993 | Hasse et al. | |
| 5,256,736 A | 10/1993 | Trepka et al. | |
| 5,260,345 A | 11/1993 | DesMarais et al. | |
| 5,269,755 A | 12/1993 | Bodicky | |
| 5,270,388 A | 12/1993 | Onishi et al. | |
| 5,296,184 A | 3/1994 | Wu | |
| 5,306,266 A | 4/1994 | Freeland | |
| 5,336,545 A | 8/1994 | Morman | |
| 5,342,338 A | 8/1994 | Roe | |
| 5,344,691 A | 9/1994 | Hanschenet et al. | |
| 5,358,500 A | 10/1994 | LaVon et al. | |
| 5,358,783 A | 10/1994 | Diehl et al. | |
| 5,387,207 A | 2/1995 | Dyer et al. | |
| 5,387,450 A | 2/1995 | Stewart | |
| 5,397,316 A | 3/1995 | LaVon et al. | |
| 5,397,318 A | 3/1995 | Dreier | |
| 5,429,856 A | 7/1995 | Krueger et al. | |
| 5,439,459 A | 8/1995 | Tanji et al. | |
| 5,439,966 A | 8/1995 | Graham et al. | |
| 5,445,140 A | 8/1995 | Tovey | |
| 5,447,508 A | 9/1995 | Numano et al. | |
| 5,468,237 A | 11/1995 | Miller et al. | |
| 5,468,428 A | 11/1995 | Hanschen et al. | |
| 5,492,751 A | 2/1996 | Butt, Sr. et al. | |
| 5,499,978 A | 3/1996 | Buell et al. | |
| 5,506,300 A | 4/1996 | Ward et al. | |
| 5,507,736 A | 4/1996 | Clear et al. | |
| 5,514,121 A | 5/1996 | Roe et al. | |
| 5,518,433 A | 5/1996 | Sneddon | |
| 5,518,801 A | 5/1996 | Chappell et al. | |
| 5,536,563 A * | 7/1996 | Shah et al. | 442/329 |
| 5,540,671 A | 7/1996 | Dreier | |
| 5,540,976 A | 7/1996 | Shawver et al. | |
| 5,545,690 A | 8/1996 | Trepka et al. | |
| 5,554,142 A | 9/1996 | Dreier et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| H1630 H | 1/1997 | Roe et al. | |
| 5,591,152 A | 1/1997 | Buell et al. | |
| 5,607,760 A | 3/1997 | Roe | |
| 5,609,587 A | 3/1997 | Roe | |
| 5,620,780 A | 4/1997 | Krueger et al. | |
| 5,625,222 A | 4/1997 | Yoneda et al. | |

| | | | | | | |
|---|---|---|---|---|---|---|
| 5,634,913 | A | 6/1997 | Stinger | 6,571,704 B2 | 6/2003 | Fujimoto et al. |
| 5,635,191 | A | 6/1997 | Roe et al. | 6,579,940 B1 | 6/2003 | Dove |
| H1670 | H | 7/1997 | Aziz et al. | 6,592,995 B2 | 7/2003 | Topolkaraev et al. |
| 5,643,588 | A | 7/1997 | Roe et al. | 6,593,430 B1 | 7/2003 | Knoll et al. |
| 5,648,167 | A | 7/1997 | Peck | 6,598,637 B2 | 7/2003 | Lechtenböhmer et al. |
| 5,653,703 | A | 8/1997 | Roe et al. | 6,626,879 B1 | 9/2003 | Ashton et al. |
| 5,669,897 | A | 9/1997 | Lavon et al. | 6,627,673 B2 | 9/2003 | Topolkaraev et al. |
| 5,691,034 | A | 11/1997 | Krueger et al. | 6,635,041 B1 | 10/2003 | Popp et al. |
| 5,714,548 | A | 2/1998 | Ma et al. | 6,648,869 B1 | 11/2003 | Gillies et al. |
| 5,719,226 | A | 2/1998 | Kegley | 6,657,000 B1 | 12/2003 | De Keyzer et al. |
| H1732 | H | 6/1998 | Johnson | 6,664,309 B2 | 12/2003 | Svenningsen et al. |
| 5,762,641 | A | 6/1998 | Bewick-Sonntag et al. | 6,664,436 B2 | 12/2003 | Topolkaraev et al. |
| 5,814,705 | A | 9/1998 | Ward et al. | 6,673,857 B1 | 1/2004 | Knoll et al. |
| 5,830,203 | A | 11/1998 | Suzuki et al. | 6,722,910 B2 | 4/2004 | Kajinuma |
| 5,853,864 | A | 12/1998 | Bunnelle | 6,746,433 B1 | 6/2004 | Shimoe et al. |
| 5,858,150 | A | 1/1999 | Yarusso et al. | 6,759,454 B2 | 7/2004 | Stephens et al. |
| 5,865,823 | A | 2/1999 | Curro | 6,759,481 B2 | 7/2004 | Tong |
| 5,889,118 | A | 3/1999 | Delgado et al. | 6,790,911 B2 | 9/2004 | Perevosnik et al. |
| 5,897,545 | A | 4/1999 | Kline et al. | 6,818,093 B1 | 11/2004 | Taal et al. |
| 5,899,895 | A | 5/1999 | Robles et al. | 6,827,806 B2 | 12/2004 | Uitenbroek et al. |
| 5,910,546 | A | 6/1999 | Trepka et al. | 6,844,383 B2 | 1/2005 | Hoshi et al. |
| 5,916,206 | A | 6/1999 | Otsubo et al. | 6,887,916 B2 | 5/2005 | Zhou et al. |
| 5,934,470 | A | 8/1999 | Bauer et al. | 6,933,421 B2 | 8/2005 | Topolkaraev et al. |
| 5,938,648 | A | 8/1999 | Lavon et al. | 6,939,906 B2 | 9/2005 | Hoshi et al. |
| 5,941,864 | A | 8/1999 | Roe | 6,946,172 B2 | 9/2005 | Munn et al. |
| 5,957,908 | A | 9/1999 | Kline et al. | 6,967,178 B2 | 11/2005 | Zhou et al. |
| 5,968,025 | A | 10/1999 | Roe et al. | 6,969,441 B2 | 11/2005 | Welch et al. |
| 5,972,519 | A | 10/1999 | Niessner et al. | 6,978,486 B2 | 12/2005 | Zhou et al. |
| 5,977,430 | A | 11/1999 | Roe et al. | 7,015,155 B2 | 3/2006 | Zhou et al. |
| 5,997,520 | A | 12/1999 | Ahr et al. | 7,056,411 B2 | 6/2006 | Desai et al. |
| 6,004,306 | A | 12/1999 | Robles et al. | 7,074,484 B2 | 7/2006 | Topolkaraev et al. |
| 6,010,490 | A | 1/2000 | Freeland et al. | 7,087,287 B2 | 8/2006 | Curro et al. |
| 6,013,063 | A | 1/2000 | Roe et al. | 7,223,261 B2 | 5/2007 | Müeller et al. |
| 6,025,071 | A | 2/2000 | Cameron et al. | 7,316,840 B2 | 1/2008 | Neculescz et al. |
| 6,031,053 | A | 2/2000 | Knoll et al. | 7,316,842 B2 | 1/2008 | Zhou et al. |
| 6,063,838 | A | 5/2000 | Patnode et al. | 2001/0004689 A1 | 6/2001 | Otsubo |
| 6,103,814 | A | 8/2000 | Vandrongelen et al. | 2002/0056384 A1 | 5/2002 | Fujimoto et al. |
| 6,107,537 | A | 8/2000 | Elder et al. | 2002/0096072 A1 | 7/2002 | Fujimoto et al. |
| 6,120,487 | A | 9/2000 | Ashton | 2002/0115744 A1 | 8/2002 | Svenningsen et al. |
| 6,120,489 | A | 9/2000 | Johnson et al. | 2002/0143313 A1 | 10/2002 | Tsuji et al. |
| 6,120,866 | A | 9/2000 | Arakawa et al. | 2002/0147273 A1 | 10/2002 | Patel et al. |
| 6,140,433 | A | 10/2000 | Zhang et al. | 2002/0165516 A1 | 11/2002 | Datta et al. |
| 6,149,637 | A | 11/2000 | Allen et al. | 2003/0088228 A1 | 5/2003 | Desai et al. |
| 6,156,842 | A | 12/2000 | Hoenig et al. | 2003/0091807 A1 | 5/2003 | Desai et al. |
| 6,168,584 | B1 | 1/2001 | Allen et al. | 2003/0111166 A1 | 6/2003 | Uitenbroek et al. |
| 6,179,820 | B1 | 1/2001 | Fernfors | 2003/0120240 A1 | 6/2003 | Buell et al. |
| 6,184,285 | B1 | 2/2001 | Goodman et al. | 2003/0233082 A1 | 12/2003 | Kline et al. |
| 6,187,696 | B1 | 2/2001 | Lim et al. | 2004/0005832 A1 | 1/2004 | Zhou et al. |
| 6,190,768 | B1 | 2/2001 | Turley et al. | 2004/0005834 A1 | 1/2004 | Zhou et al. |
| 6,193,701 | B1 | 2/2001 | Van Gompel et al. | 2004/0005835 A1 | 1/2004 | Zhou et al. |
| 6,194,073 | B1 | 2/2001 | Li et al. | 2004/0006324 A1 | 1/2004 | Zhou et al. |
| 6,197,889 | B1 | 3/2001 | Knoll et al. | 2004/0013852 A1 | 1/2004 | Curro et al. |
| 6,211,272 | B1 | 4/2001 | Hansen et al. | 2004/0092900 A1* | 5/2004 | Hoffman et al. .............. 604/380 |
| 6,235,847 | B1 | 5/2001 | Hoshi et al. | 2004/0092902 A1 | 5/2004 | Hoffman et al. |
| 6,245,050 | B1 | 6/2001 | Odorzynski et al. | 2004/0123938 A1 | 7/2004 | Zhou et al. |
| 6,265,484 | B1 | 7/2001 | Trepka et al. | 2004/0127881 A1* | 7/2004 | Stevens et al. ........... 604/385.22 |
| 6,265,485 | B1 | 7/2001 | Trepka et al. | 2004/0162536 A1 | 8/2004 | Becker |
| 6,274,666 | B1 | 8/2001 | Dougherty | 2004/0162538 A1 | 8/2004 | Mueller et al. |
| 6,274,685 | B2 | 8/2001 | Blok et al. | 2004/0167486 A1 | 8/2004 | Busam |
| 6,288,149 | B1 | 9/2001 | Kroll | 2004/0181200 A1 | 9/2004 | Desai et al. |
| 6,300,208 | B1 | 10/2001 | Talwar et al. | 2004/0182499 A1 | 9/2004 | Zhou et al. |
| 6,310,154 | B1 | 10/2001 | Babcock et al. | 2004/0193134 A1 | 9/2004 | Mueller et al. |
| 6,357,499 | B1 | 3/2002 | Kralevich, Jr. et al. | 2004/0222553 A1 | 11/2004 | Desai et al. |
| 6,369,160 | B1 | 4/2002 | Knoll et al. | 2005/0095942 A1 | 5/2005 | Mueller |
| 6,372,853 | B1 | 4/2002 | Li et al. | 2005/0096416 A1 | 5/2005 | Zhou et al. |
| 6,383,431 | B1 | 5/2002 | Dobrin et al. | 2005/0170729 A1 | 8/2005 | Stadelman et al. |
| 6,418,848 | B1 | 7/2002 | Fujimoto et al. | 2005/0171499 A1 | 8/2005 | Nigam et al. |
| 6,419,798 | B1 | 7/2002 | Topolkaraev et al. | 2005/0177123 A1 | 8/2005 | Catalan |
| 6,423,807 | B1 | 7/2002 | Oi et al. | 2005/0211368 A1 | 9/2005 | McGuire |
| 6,432,098 | B1 | 8/2002 | Kline et al. | 2005/0215963 A1 | 9/2005 | Autran et al. |
| 6,444,755 | B1 | 9/2002 | Deporter et al. | 2005/0215972 A1 | 9/2005 | Roe et al. |
| 6,455,627 | B1 | 9/2002 | De Keyzer et al. | 2005/0215973 A1 | 9/2005 | Roe et al. |
| 6,476,288 | B1 | 11/2002 | Vanrijswijck et al. | 2005/0256476 A1 | 11/2005 | Mirle et al. |
| 6,482,191 | B1 | 11/2002 | Roe et al. | 2005/0273072 A1 | 12/2005 | Hird et al. |
| 6,485,557 | B1 | 11/2002 | Swiler | 2006/0003656 A1 | 1/2006 | Morman |
| 6,521,704 | B1 | 2/2003 | Hubbard et al. | 2006/0004342 A1 | 1/2006 | Sawyer et al. |
| 6,531,544 | B1 | 3/2003 | Vaughan et al. | 2006/0058765 A1 | 3/2006 | Mueller |
| 6,533,987 | B2 | 3/2003 | Topolkaraev et al. | 2006/0078042 A1 | 4/2006 | Lee |
| 6,565,549 | B1 | 5/2003 | Allen et al. | 2006/0083900 A1 | 4/2006 | Ashraf |

| | | | |
|---|---|---|---|
| 2006/0155255 | A1 | 7/2006 | McKiernan et al. |
| 2006/0167434 | A1 | 7/2006 | Ashton et al. |
| 2006/0264858 | A1 | 11/2006 | Roe et al. |
| 2007/0037907 | A9 | 2/2007 | Zhou et al. |
| 2007/0088307 | A1 | 4/2007 | Arizti |
| 2007/0093771 | A1 | 4/2007 | Arizti |
| 2007/0191806 | A1 | 8/2007 | Mueller |
| 2007/0197993 | A1 | 8/2007 | Arizti |
| 2007/0197994 | A1 | 8/2007 | Arizti |
| 2008/0033388 | A1 | 2/2008 | Mueller |
| 2008/0108963 | A1 | 5/2008 | Ashton et al. |
| 2008/0195070 | A1 | 8/2008 | Ponomarenko |

FOREIGN PATENT DOCUMENTS

| | | | |
|---|---|---|---|
| DE | 1910911 | | 3/1969 |
| EP | 0119827 | | 7/1988 |
| EP | 0316671 | | 11/1988 |
| EP | 0433951 | | 6/1991 |
| EP | 0591647 | | 4/1994 |
| EP | 0597331 | | 5/1994 |
| EP | 0451919 | | 2/1995 |
| EP | 0 650 714 A | | 5/1995 |
| EP | 0847738 | | 6/1998 |
| EP | 1351815 | | 2/2005 |
| EP | 1013291 | * | 6/2005 |
| EP | 1226018 | * | 10/2005 |
| GB | 2297473 | * | 8/1995 |
| GB | 2287888 | * | 10/1995 |
| GB | 2328158 | * | 2/1999 |
| GB | 2329842 | * | 4/1999 |
| JP | 62241944 | * | 10/1987 |
| JP | 63238153 | * | 10/1988 |
| JP | 3160083 | * | 7/1991 |
| JP | 3160084 | * | 7/1991 |
| JP | 3239738 | * | 10/1991 |
| JP | 4153288 | * | 5/1992 |
| JP | 7157738 | * | 6/1995 |
| JP | 8060120 | * | 3/1996 |
| JP | 8060121 | * | 3/1996 |
| JP | 8277382 | * | 10/1996 |
| JP | 8281764 | * | 10/1996 |
| JP | 9291265 | * | 11/1997 |
| JP | 9302319 | * | 11/1997 |
| JP | 2000282006 | * | 5/1999 |
| JP | 11279521 | * | 10/1999 |
| JP | 2001040302 | * | 2/2001 |
| JP | 2001279212 | * | 10/2001 |
| JP | 2001293789 | * | 10/2001 |
| WO | WO 94/14395 | | 7/1994 |
| WO | WO 95/16746 | | 6/1995 |
| WO | WO 96/11236 | * | 4/1996 |
| WO | WO 96/23823 | * | 8/1996 |
| WO | WO 98/08476 | * | 3/1998 |
| WO | WO 99/13016 | * | 3/1999 |
| WO | WO 99/45880 | * | 9/1999 |
| WO | WO 00/12645 | * | 3/2000 |
| WO | WO 00/22061 | * | 4/2000 |
| WO | WO 00/30581 | * | 4/2000 |
| WO | WO 00/69834 | * | 11/2000 |
| WO | WO 01/87589 A | | 11/2001 |
| WO | WO 02/33578 | | 4/2002 |
| WO | WO 02/083786 | | 10/2002 |
| WO | WO 03/047488 A | | 6/2003 |
| WO | WO 03/082571 A | | 10/2003 |
| WO | WO 2006/074481 | | 7/2006 |

OTHER PUBLICATIONS

U.S. Appl. No. 10/171,249, filed Jun. 13, 2002, Kline et al.
U.S. Appl. No. 11/055,743, filed Feb. 10, 2005, Catalan.
U.S. Appl. No. 60/643,920, filed Jan. 10, 2005, Roe et al.
U.S. Appl. No. 11/145,353, filed Jun. 3, 2005, McKieman et al.
Polymer Handbook, Wiley Interscience; Section VII, $3^{rd}$ Edition, pp. 519-559, USA.
U.S. Appl. No. 11/144,508, filed Jun. 3, 2005, Office Action dated May 18, 2007.
U.S. Appl. No. 11/144,508, filed Jun. 3, 2005, Office Action dated Jul. 16, 2008.
U.S. Appl. No. 11/145,353, filed Jun. 3, 2005, Office Action dated Dec. 11, 2007.
U.S. Appl. No. 11/145,353, filed Jun. 3, 2005, Office Action dated Jul. 30, 2008.
Ziabicki, *Fundamentals of Fibre Formation*, John Wiley & Sons, New York (1976), Chapter 6.
J.H. Briston, *Plastic Films*, $2^{nd}$ Edition, Longman Inc., New York (1983), pp. 83-85.
I.M. Ward, *Mechanical Properties of Solid Polymers*, Wiley-Interscience, New York (1971), p. 278.
U.S. Appl. No. 11/144,508, filed Jun. 3, 2005, Herd et al., Office Action dated Mar. 16, 2009.
U.S. Appl. No. 11/144,508, filed Jun. 3, 2005, Herd et al., Office Action dated Jul. 16, 2008.
U.S. Appl. No. 11/144,508, filed Jun. 3, 2005, Herd et al., Office Action dated May 18, 2007.
U.S. Appl. No. 11/145.353, filed Jun. 3, 2005, McKiernan et al., Office Action dated Feb. 10, 2009.
U.S. Appl. No. 11/145,353, filed Jun. 3, 2005, McKiernan et al., Office Action dated Jul. 30, 2008.
U.S. Appl. No. 11/145,353, filed Jun. 3, 2005, McKiernan et al., Office Action dated Dec. 11, 2007.
U.S. Appl. No. 11/340,803, filed Jan. 26, 2006, Ashton et al., Office Action dated Apr. 7, 2009.
U.S. Appl. No. 11/340,803, filed Jan. 26, 2006, Ashton et al., Office Action dated Dec. 16, 2008.
U.S. Appl. No. 11/340,803, filed Jan. 26, 2006, Ashton et al., Office Action dated Jun. 18, 2008.

* cited by examiner

ABSORBENT ARTICLES COMPRISING A SLOW RECOVERY STRETCH LAMINATE

CROSS REFERENCE TO RELATED APPLICATION

This application claims the benefit of U.S. Provisional Application Nos. 60/577,037, filed Jun. 4, 2004, and 60/643,920, filed Jan. 10, 2005.

FIELD OF THE INVENTION

This invention is directed to absorbent articles such as diapers, training pants, adult incontinence articles, feminine hygiene articles, and the like comprising a slow recovery stretch laminate.

BACKGROUND OF THE INVENTION

Stretch laminates are well known in the art. It has long been known in the field of disposable absorbent articles that it is desirable to construct absorptive devices, such as disposable diapers with fasteners, pull-on diapers, training pants, sanitary napkins, pantiliners, incontinence briefs, and the like, with stretch laminates to improve the ease of motion and maintenance of a sustained fit. Furthermore, stretch laminates allow the diaper to accommodate a range of different sized wearers. A diaper may have stretch laminates in a number of its structures including the waist band, leg cuffs, side panels, elasticized topsheets, backsheet, ears, and fastening system.

During application, a diaper generally may be stretched and elongated longitudinally and/or laterally from its initial substantially compacted and untensioned state. Upon release of the elongating tension, the diaper often contracts, constricts, and/or folds before it can be successfully applied to or adjusted on a wearer. In traditional taped diapers, the stretch laminates, which may be present in a leg cuff, may require elongation prior to application onto a wearer. However, if a continuous force is not maintained, the stretch laminates within the leg cuff may cause the diaper to retract quickly. Generally, a caregiver needs to apply a continuous elongating force to the diaper while at the same time positioning the diaper onto the wearer and tending to the wearer who may be uncooperative (e.g., crying, fussing, moving, resisting, etc.) during the diapering process. These multiple simultaneous requirements can lead to frustration for the caregiver. The multiple simultaneous requirements may result in the diaper being positioned improperly on the wearer.

Similarly, in pant-type articles, the stretch laminates, which may be present in a waist feature or side panel, may require elongation so as to enlarge the waist opening from an initial constrictive and untensioned state. A continuous force may need to be applied during the application process, generally by a caregiver or wearer, to counteract the rapid retraction of the stretch laminates that would be experienced otherwise. Leg openings in pants-type articles commonly incorporate stretch laminates and may also tend to retract quickly thereby increasing the difficulty of pulling the article up to the desired location on the wearer's lower torso. Applying a continuous force to maintain an enlarged waist opening may be difficult for young children who lack the hand strength and dexterity to apply the continuous force while simultaneously pulling on the pant. Likewise, elderly individuals may also lack the necessary hand strength and dexterity to apply a continuous force while simultaneously pulling on an incontinence article.

Furthermore, recent diaper advancements have focused on the acceptance and storage of feces. In conventional diaper designs, feces remain between the diaper's topsheet and the wearer's skin. As a result, the wearer experiences excessive soiling, irritation, and the potential of leakage generally around the leg cuff. Advances in diaper design include the use of an apertured elasticized topsheet to isolate feces away from the wearer's skin thus preventing leakage and irritation. The apertured elasticized topsheet forms a void between the elasticized topsheet and the underlying diaper structure. A stretch laminate generally is associated with the elasticized topsheet to aid in keeping the elasticized topsheet substantially in contact with the wearer's skin. Furthermore, the stretch laminate aids in keeping the aperture positioned so that the underlying diaper structure may receive the fecal insult.

While elasticized topsheets are conceptually advantageous, diapers with elasticized topsheets comprising conventional elastomers are often difficult to apply. Application of the diaper requires a caregiver to stretch the diaper so that it is in a substantially planar position. Upon release, the stretch laminate contracts at a rate that makes it difficult for the caregiver to position the diaper correctly onto the wearer. This "snap-back" of the elasticized topsheet may increase the difficulty of applying the diaper to the wearer. If the diaper is difficult to apply, there may be a tendency for mispositioning the aperture, which may result in fecal deposit on the elasticized topsheet rather than through the aperture. Mispositioning of the aperture can destroy the benefit of isolating feces from the wearer's skin. Examples of diapers comprising an elasticized topsheet having an aperture have been disclosed in U.S. Pat. No. 4,892,536, issued to Des Marais et al. and U.S. Pat. No. 4,990,147 issued to Freeland.

Thus, there is a need for an absorbent product comprising a stretch laminate that retracts slowly upon being released from a stretched state, thus facilitating application and positioning of the product correctly onto the wearer.

One problem that exists in filling the need for a stretch laminate that retracts slowly upon release from a stretched state is that stretch laminates is generally an inhomogenous material. Stretch laminates generally may include an elastic member and a relatively inelastic substrate. The elastic member and the substrate may be joined by bonding techniques known in the art such as by an adhesive. It is the combination of these materials as a laminate that must result in the slow recovery. Furthermore, the formation technique can affect the recovery characteristics of the resultant stretch laminate. For example, a stretch bonded laminate involves joining a strained elastic member to a substantially inelastic substrate. Upon release of the strain force, the elastic member retracts and may gather the substrate. The initial strain of the elastic member can impact the extendibility and the recovery characteristic of the stretch laminate. The construction and basis weight of the substrate may also impact the recovery characteristic of the stretch laminate.

SUMMARY OF THE INVENTION

In response to the problems identified above, the present invention provides an absorbent article comprising a topsheet, a backsheet joined with the topsheet, an absorbent core interposed between the topsheet and backsheet; and one or more article elements selected from the group consisting of an anal cuff, an elasticized topsheet, a fastening system, a leg cuff, a waist elastic feature, a side panel, an ear, and combinations thereof. The article element may comprise a slow recovery stretch laminate exhibiting an unload force at 37° C.

of about 0.16 N/(g/m) or greater and a percent of initial strain after 15 seconds of recovery at 22° C. of about 10% or greater.

The present invention also provides for a slow recovery stretch laminate comprising at least a first substrate having a first surface and a second surface, and at least one elastic member joined to the first surface of the substrate. The slow recovery stretch laminate exhibits an unload force at 37° C. of about 0.16 N/(g/m) or greater and a percent of initial strain after 15 seconds of recovery at 22° C. of about 10% or greater. The slow recovery stretch laminate may be incorporated into an absorbent article or a medical product.

The present invention also provides for an absorbent article comprising a topsheet, a backsheet joined with the topsheet, an absorbent core interposed between the topsheet and backsheet, and a slow recovery stretch laminate. The slow recovery stretch laminate comprises at least a first substrate having a first surface and a second surface and at least one elastic member joined to the first surface of the substrate. The slow recovery stretch laminate exhibits an unload force at 37° C. of about 0.16 N/(g/m) or greater and a percent of initial strain after 15 seconds of recovery at 22° C. of about 10% or greater.

The present invention provides an absorbent article comprising a topsheet, a backsheet joined with the topsheet, an absorbent core interposed between the topsheet and backsheet; and one or more article elements selected from the group consisting of an anal cuff, an elasticized topsheet, a fastening system, a leg cuff, a waist elastic feature, a side panel, an ear, and combinations thereof. The article element may comprise a slow recovery stretch laminate exhibiting an unload force at 37° C. of about 0.16 N/(g/m) or greater. The slow recovery stretch laminate may exhibit a percent strain after 15 seconds of recovery at 22° C. of about 10% or greater when tested at an initial strain of 100% or less.

DETAILED DESCRIPTION OF THE PRESENT INVENTIONS

Figure 1A:
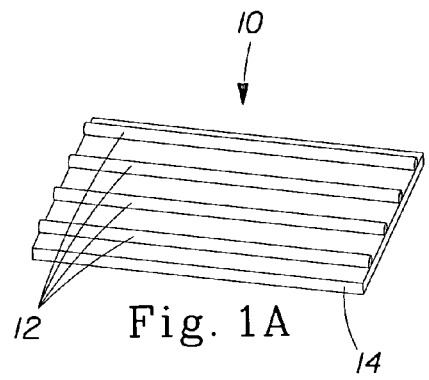
FIGS. 1A-E are perspective views of embodiments of the slow recovery stretch laminate.

As used herein, the term "absorbent article" or "article" refers to a wearable device that absorbs and/or contains liquid and, more specifically, refers to a device that is placed against or in proximity to the body of the wearer to absorb and contain the various exudates discharged from the body. Suitable examples include diapers, training pants, pull-on garments, adult incontinence products and feminine care products such as sanitary napkins. Furthermore, "absorbent article" includes "disposable absorbent article" which is intended to be discarded and not laundered or otherwise restored after no more than ten uses, preferably after no more than five uses, and most preferably after a single use (although certain components may be recycled, reused, or composted).

As used herein, the term "stretch laminate" generally refers to an elastomer which is attached to at least one material such as a polymeric film, a nonwoven, a woven, or a scrim. The elastomer may be attached to the material by any of a number of bonding methods known to those skilled in the art, including adhesive bonding, thermal bonding, pressure bonding, ultrasonic bonding, and the like. A stretch laminate is generally able to extend to a strain of at least 50% without breaking or rupturing, and is able to recover substantially to its original dimensions after the deforming force has been removed.

As used herein, the term "laminate" refers to a material comprising two or more layers. The term includes stretch laminates and non-stretch laminates.

As used herein, the term "diaper" refers to an absorbent article generally worn by infants and incontinent persons about the lower torso.

As used herein, the term "substrate" refers to a material that is laminated to the elastic member to form the stretch laminate. Suitable substrates include nonwoven webs, woven webs, knitted fabrics, films, film laminates, apertured films, nonwoven laminates, sponges, foams, scrims, and any combinations thereof. Suitable substrates may comprise natural materials, synthetic materials, or any combination thereof.

As used herein, the term "longitudinal" generally means a direction running parallel to the longitudinal axis, of the article and includes directions within 45° of the longitudinal direction.

As used herein, the term "length" of the article or component thereof generally refers to the size/distance of the maximum linear dimension, or typically to the size/distance of the longitudinal axis, or an article or part thereof.

As used herein, the terms "lateral" or "transverse" refer to a direction generally orthogonal to the longitudinal direction and parallel to the transverse axis.

As used herein, the term "width" of the article or of a component thereof refers to the size/distance of the dimension orthogonal to the longitudinal direction of the article or component thereof, e.g. orthogonal to the length of the article or component thereof, and typically it refers to the distance/size of the dimension parallel to the transverse axis of the article or component.

As used herein, the term "attached" encompasses configurations whereby an element is directly secured to another element by affixing the element directly to the other element.

As used herein, the term "joined" or "connected" encompasses configurations whereby a first element is directly secured to second element by affixing the first element directly to the second element and configurations whereby a first element is indirectly secured to a second element by affixing the first element to intermediate member(s), which in turn are affixed to the second element. "Joined" or "connected" elements may be affixed either continuously or intermittently.

As used herein, "relaxed" or "relaxed state" means the state where no forces are applied to an article (other than naturally occurring forces such as gravity).

As used herein, the terms "extendibility" and "extensible", e.g. extendibility of the elastomer, mean that the width or length of the item in the relaxed position can be extended or increased.

As used herein, "elasticated" or "elasticized" means that the component comprises at least a portion made of elastic material.

As used herein, the terms "elastic," "elastomer," and "elastomeric" refer to a material which generally is able to extend to a strain of at least 50% without breaking or rupturing, and is able to recover substantially to its original dimensions after the deforming force has been removed.

As used herein, the term "medical product" means surgical gowns and drapes, face masks, head coverings, shoe coverings, wound dressings, bandages and sterilization wraps as disclosed in U.S. Pat. No. 5,540,976.

As used herein, the term "copolymer" refers to a polymer synthesized from two or more monomers with different chemical structures.

As used herein, the terms "temperature responsive" and "temperature responsiveness" refer to a slow recovery stretch laminate exhibiting less post elongation strain after a specified amount of time at higher temperatures than at lower temperatures.

As used herein, the term "conventional stretch laminate" refers to a stretch laminate that exhibits a minimal percent of initial strain after 15 seconds of recovery at 22° C. as measured by the Post Elongation Recovery Test. Conventional stretch laminates exhibit a percent of initial strain after 15 seconds of recovery at 22° C. of less than 10%, as measured by the Post Elongation Recovery Test.

As used herein, the term "percent of initial strain" refers to the percentage of initial strain remaining after some period of time after release from that initial strain as measured by the Post Elongation Recovery Test. "Percent of initial strain" is calculated by dividing the percent strain at a given time after release from an initial strain by the initial percent strain; the quotient is multiplied by 100 to yield a percentage.

The absorbent article of the present invention comprises a slow recovery stretch laminate (SRSL). The SRSL may be used within the absorbent article wherever elastic properties are desired. The SRSL generally comprises an elastic member joined to a substrate. The SRSL may be formed discretely and joined with the absorbent article. Conversely, the SRSL may be integral to the absorbent article (e.g., an elastic member is joined to an existing substrate in the absorbent article such as the topsheet to form a stretch laminate). The elastic member may be prepared from a composition comprising an elastomeric polymer, optionally at least one modifying resin, and optionally one or more additives. The SRSL exhibits a normalized unload force at 37° C. of at least about 0.16 N/(g/m) as measured by the Two Cycle Hysteresis Test described below. The SRSL exhibits a percent of initial strain after 15 seconds of recovery at 22° C. of about 10% or greater, as measured by the Post Elongation Recovery Test as described below.

In another embodiment of the present invention, the SRSL may be incorporated into a medical product such as a surgical gown, a face mask, a head covering, a shoe covering, a wound dressing, a bandage, or a sterilization wrap. The SRSL may be used in the medical products at locations where an elastic character is desired.

As shown in FIGS. 1A-E, the SRSL 10 generally comprises an elastic member 12 joined to a substrate 14. Joining of the elastic member 12 and the substrate 14 may be conducted by a variety of bonding methods such as heat bonds, pressure bonds, ultrasonic bonds, mechanical bonds, adhesive bonds, or any other suitable attachment means or combinations of these attachment means as are known in the art. In certain embodiments, the elastic member 12 may exhibit sufficient tack to join the elastic member 12 and the substrate 14.

The elastic members 12 having a variety of forms may be used in the SRSL 10. Suitable forms for the elastic members 12 include, but are not limited to films, bands, strands, individualized fibers, scrims, cross-hatch arrays, foams, or combinations thereof.

Figure 1B:
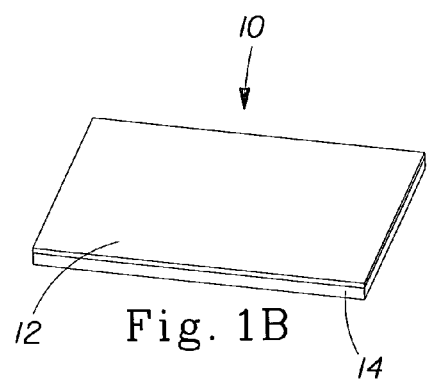
Figure 1C:
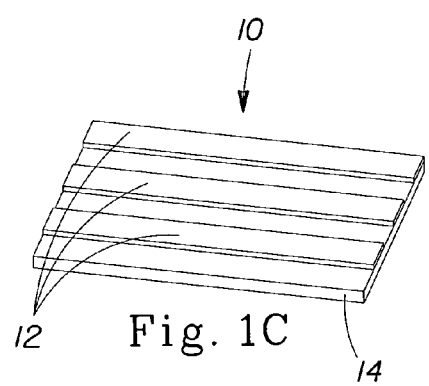

FIGS. 1A-E depict several suitable embodiments of the SRSL 10. FIG. 1A depicts a SRSL 10 having one or more elastic members 12 in the form of bands or ribbons joined with a substrate 14. FIG. 1B depicts a SRSL 10 having a sheet-like elastic member 12 joined with a sheet-like substrate 14. The elastic member 12 and the substrate 14 are shown as being coterminous; however, either layer may have dimensions differing from the other layer. FIG. 1C depicts a SRSL 10 having one or more elastic members 12 in the form of strands joined with a substrate 14.

Figure 1D:
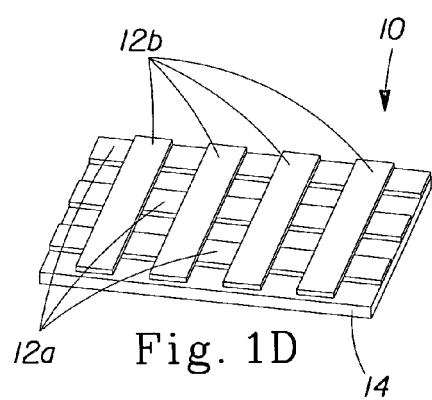
Figure 1E:
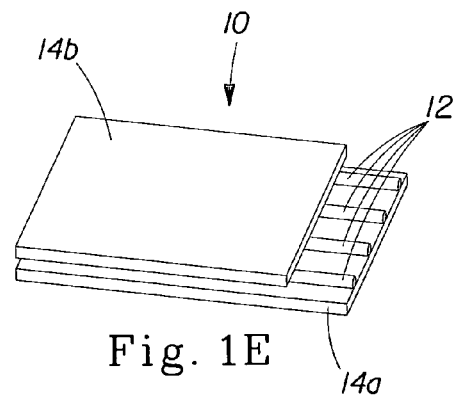

FIG. 1D depicts a SRSL 10 having one or more elastic members in the form of a cross-hatch array joined with a substrate 14. A cross-hatch array may be formed in one instance by joining a plurality of elastic members 12a in parallel to the substrate 14. A second plurality of elastic members 12b may be joined in parallel to the substrate. The second plurality 12b may be joined in a non-parallel configuration to the first plurality 12a. A cross-hatch array may also be formed by hot needle punching of an elastomeric film. A cross-hatch array may also be formed from a porous, macroscopically-expanded, three-dimensional elastomeric web as described in U.S. Patent Application Publication No. 2004/0013852. The publication describes how the cross-hatch array can be achieved by forming the film on a porous forming structure and applying a fluid pressure differential across the thickness of the film. The fluid pressure differential causes the film to conform to the supporting structure and rupture thereby creating a cross-hatch array. FIG. 1E depicts a SRSL 10 having one or more elastic members 12 joined to two or more substrates: first substrate 14a and second substrate 14b. The particular order of the SRSL 10 layers can vary; however, in the embodiment depicted, the elastic members 12 are disposed between the first substrate 14a and the second substrate 14b, and may be bonded to one or both. The first and second substrate 14a, 14b may comprise the same material or may be distinct.

The techniques for the formation of stretch laminates are well known in the art, and these techniques may be applicable in the formation of the SRSL 10 of the present invention. One technique for creating a stretch laminate, which is commonly known as "stretch bonding," involves an elastic member such as elastic strands, bands, ribbons, films, or the like being joined to a substrate while the elastic member is in a stretched configuration. Generally, the elastic member may be stretched to at least 25% of its relaxed length. After joining, the elastic member is allowed to relax thereby gathering the substrate and creating a stretch laminate.

Another technique for creating a stretch laminate, which is commonly known as "neck bonding," involves an elastic member being bonded to a substrate while the substrate is extended and necked. In certain embodiments, the substrate may be a non-elastic substrate. Examples of neck-bonded laminates are described in U.S. Pat. Nos. 5,226,992; 4,981,747; 4,965,122; and 5,336,545. A variant of "neck bonding" is "neck stretch bonding." Neck stretch bonding refers to an elastic member being bonded to a substrate while the substrate is extended and necked and the elastic member is extended. Examples of necked stretch bonded laminates are described in U.S. Pat. Nos. 5,114,781 and 5,116,662.

In another technique for forming a stretch laminate, elastic members can be attached to a substrate in either a relaxed configuration or partially stretched configuration. The resulting laminate can be made stretchable (or more stretchable in the case of partially stretched strands or film) by subjecting the laminate to an elongation process which elongates the substrate permanently, but elongates the elastic members only temporarily. Such processes are known in the art as "zero strain" stretch laminate formation, and the elongation of such laminates may be accomplished with suitable means such as rollers, engaging teeth, or the like. Examples of zero strain activation processing and formations of resulting stretch laminates are described in U.S. Pat. Nos. 5,167,897 and 5,156,793

An alternate technique for the formation of a stretch laminate is disclosed in U.S. Patent Application Publication Nos. 2003/0088228A1, 2003/0091807A1, and 2004/0222553A1. The technique disclosed in these publications involves forming the elastic member by hot melt application of one or more thermoplastic elastomers onto a substrate, followed by incremental stretching of the substrate that confers the stretch properties of the elastomer to the substrate. Suitable application methods include, for example, direct gravure, offset gravure, and flexographic printing. Each of these methods allows deposition of an amount of elastomer in any shape and direction, thus providing substantial flexibility in the stretch character exhibited by the stretch laminate. Other conventional methods for stretch laminate formation are within the scope of this description.

The elastic member 12 may comprise an elastomeric polymer, optionally at least one modifying resin, and optionally one or more additives. A number of elastomeric polymers, either alone or in combination, can be used to prepare the elastic member 12. Elastomeric polymers include, but are not limited to, homopolymers (e.g., crosslinked poly(isoprene)), block copolymers, random copolymers, alternating copolymers, and graft copolymers. Suitable elastomeric polymers comprise styrenic block copolymers, natural and synthetic rubbers, polyisoprene, neoprene, polyurethanes, silicone rubbers, hydrocarbon elastomers, ionomers, and the like.

In one embodiment, the elastomeric polymer may be a block copolymer. A number of block copolymers may be used including multi-block, tapered block and star block copolymers. Generally, the block copolymers suitable for use in the present invention may exhibit both elastomeric and thermoplastic characteristics. In such block copolymers a hard block (or segment) may have a glass transition temperature (Tg) greater than about 25° C. or is crystalline or semicrystalline with a melting temperature (Tm) above about 25° C. Preferably, the hard block has a Tg greater than about 35° C. or is crystalline or semicrystalline with a Tm above about 35° C. The hard block portion is typically derived from vinyl monomers including vinyl arenes such as styrene and alpha-methyl-styrene or combinations thereof.

Glass transition temperatures referred to herein are determined by tensile dynamic mechanical analysis performed in the linear elastic region of the material at a frequency of 1 Hz using a temperature ramp method. Suitably, film samples with a uniform thickness of about 0.3 mm may be used with a temperature ramp rate of about 1° C./min or slower. The Tan δ peak temperature is taken as the Tg of the particular material or phase.

Crystalline melting temperatures referred to herein are determined by Differential Scanning Calorimetry using a temperature ramp rate of 10° C./min. The melting endothermic peak temperature is taken as the Tm of the particular crystalline region.

The block copolymers may comprise a soft block (or segment). The soft block generally exhibits a sufficiently low glass transition temperature and/or melting temperature so as not to form glassy or crystalline regions at the use temperature of the copolymer. In one embodiment, the use temperature may be between about room temperature (about 22° C.) and about body temperature (about 37° C.). However, other use temperatures are feasible and within the scope of this invention. Such soft blocks are generally physically incompatible with the hard blocks and form separate regions, domains, or phases.

The soft block portion may be a polymer derived from conjugated aliphatic diene monomers. Typically, the monomers use to synthesize the soft block contain fewer than about 6 carbon atoms. Suitable diene monomers include butadiene, isoprene, and the like. Particularly preferred soft block polymers include poly(butadiene) and poly(isoprene). Furthermore, it is envisioned that the soft block may be modified to tailor the Tg of the soft block. For example, a random copolymer of isoprene and styrene or a graft of styrene onto poly(isoprene) may be used. In such cases, lower amounts of the modifying resin may be used.

Suitable block copolymers for use in this invention may comprise at least one hard block (A) and at least one soft block (B). The block copolymers may have multiple blocks. In a preferred embodiment, the block copolymer may be an A-B-A triblock copolymer, an A-B-A-B tetrablock copolymer, or an A-B-A-B-A pentablock copolymer. Also, useful herein are triblock copolymers having endblocks A and A', wherein A and A' may be derived from different vinyl compounds. Also, useful in the present invention are block copolymers having more than one hard block and/or more than one soft block, wherein each hard block may be derived from the same or different monomers and each soft block may be derived from the same or different monomers. It should be noted that where the copolymer contains residual olefinic double bonds, the copolymer may be partially or fully hydrogenated if desired. Saturation may often yield beneficial effects in the elastomeric properties of the copolymer.

The elastic member 12 generally may comprise the elastomeric polymer in amounts from about 20% to about 100%, by weight. In other suitable embodiments, the elastic member 12 generally may comprise the elastomeric polymer in amounts from about 30% to about 65%. Alternatively, the elastic member 12 generally may comprise the elastomeric polymer in amounts from about 45% to about 60%.

In suitable embodiments, elastomeric polymers include styrene-olefin-styrene triblock copolymers such as styrene-butadiene-styrene (S-B-S), styrene-ethylene/butylene-styrene (S-EB-S), styrene-ethylene/propylene-styrene (S-EP-S), styrene-isoprene-styrene (S-I-S), hydrogenated polystyrene-isoprene/butadiene-styrene (S-EEP-S), and mixtures thereof. The block copolymers may be employed alone or in a blend of block copolymers.

In particular embodiments, the elastomeric polymers include styrene-butadiene-styrene (S-B-S) and styrene-isoprene-styrene (S-I-S) block copolymers. Such linear block copolymers of styrene-butadiene-styrene (S-B-S) and styrene-isoprene-styrene (S-I-S) are commercially available under the trade designation Vector from Dexco Polymers L.P., Houston, Tex., and under the trade designation Kraton from Kraton Polymers, Houston, Tex.

The elastic member 12 may comprise one or more modifying resins. Suitable modifying resins should preferably associate or phase mix with the soft blocks of the elastomeric polymer. The elastic member 12 may comprise modifying resins in amounts from about 0% to about 60% by weight. In other embodiments, the elastic member 12 may comprise modifying resins in amounts from about 20% to about 55%. In certain embodiments, the elastic member 12 may comprise modifying resins in amounts from about 40% to about 50%.

Suitable modifying resins useful herein may have glass transition temperatures ranging from about 60° C. to about 180° C., more preferably from about 70° C. to about 150° C., and more preferably from about 90° C. to about 130° C.

Suitable modifying resins may be soft block associating. A solubility parameter is useful in determining whether the modifying resin will phase mix with the soft block of the block copolymer. Generally, modifying resins are selected so that the solubility parameter of the modifying resin is similar to the solubility parameter of the soft block phase. For example in the case where the solubility parameter of the soft block phase is about 8 $(cal/cm^3)^{1/2}$, the solubility parameter of the modifying resin may be from about 7.5 $(cal/cm^3)^{1/2}$ to about 8.5 $(cal/cm^3)^{1/2}$. The solubility parameters of the modifying resins may also approximate the solubility of the hard block. However, so long as the modifying resin phase mixes with the soft block, hard block phase mixing should not be read as limiting. A list of solubility parameters for common polymers or resins, along with methods for determining or approximating the solubility parameters can be found in the *Polymer Handbook*, Third Edition; Wiley Interscience; Section VII pages 519-559.

Modifying resins useful herein include, but are not limited to, unhydrogenated C5 hydrocarbon resins or C9 hydrocarbon resins, partially and fully hydrogenated C5 hydrocarbon resins or C9 hydrocarbon resins; cycloaliphatic resins; terpene resins; polystyrene and styrene oligomers; poly(t-butylstyrene) or oligomers thereof; rosin and rosin derivatives; coumarone indenes; polycyclopentadiene and oligomers thereof; polymethylstyrene or oligomers thereof; phenolic resins; indene polymers, oligomers and copolymers; acrylate and methacrylate oligomers, polymers, or copolymers; derivatives thereof; and combinations thereof. Preferably, the resin is selected from the group consisting of the oligomers, polymers and/or copolymers derived from: t-butylstyrene, cyclopentadiene, iso-bornyl methacrylate, methyl methacrylate, isobutyl methacrylate, indene, coumarone, vinylcyclohexane, methylstyrene, and 3,3,5-trimethylcyclohexyl methacrylate. Preferred modifying resins also include alicyclic terpenes, hydrocarbon resins, cycloaliphatic resins, poly-beta-pinene, terpene phenolic resins, and combinations thereof. "C5 hydrocarbon resins" and "C9 hydrocarbon resins" are disclosed in U.S. Pat. No. 6,310,154.

The elastic member 12 may comprise a variety of additives. Suitable additives include, for example, stabilizers, antioxidants, and bacteriostats may be employed to prevent thermal, oxidative, and bio-chemical degradation of the elastic member 12. Generally, additives may account for about 0.01% to about 60% of the total weight of the elastic member 12. In other embodiments, the composition comprises from about 0.01% to about 25%. In other suitable embodiments, the composition comprises from about 0.01% to about 10% by weight, of additives.

Various stabilizers and antioxidants are well known in the art and include high molecular weight hindered phenols (i.e., phenolic compounds with sterically bulky radicals in proximity to the hydroxyl group), multifunctional phenols (i.e., phenolic compounds with sulfur and phosphorous containing groups), phosphates such as tris-(p-nonylphenyl)-phosphite, hindered amines, and combinations thereof. Proprietary commercial stabilizers and/or antioxidants are avalaible under a number of trade names including a variety of Wingstay®, Tinuvin® and Irganox® products.

The elastic member 12 may comprise various bacteriostats are known in the art. Examples of suitable bacteriostats include benzoates, phenols, aldehydes, halogen containing compounds, nitrogen compounds, and metal-containing compounds such as mercurials, zinc compounds and tin compounds. A representative is available under the trade designation Irgasan PA from Ciba Specialty Chemical Corporation, Tarrytown, N.Y.

Other optional additives include thermoplastic polymers or thermoplastic polymer compositions which preferentially associate with the hard blocks or segments of the block copolymers. Without intending to be bound by theory, it is believed that these thermoplastic polymers become incorporated into the entangled three-dimensional network structure of the hard phase. This entangled network structure can provide improved tensile, elastic and stress relaxation properties of the elastomeric composition. When the elastomeric polymer comprises a styrenic block copolymer, thermoplastic polymer additives such as polyphenylene oxide and vinylarene polymers derived from monomers including styrene, alpha-methyl styrene, para-methyl styrene, other alkyl styrene derivatives, vinyl toluene, and mixtures thereof, are useful in the present invention because they are generally considered to be chemically compatible with the styrenic hard blocks of the block copolymer.

The elastic member 12 may comprise viscosity modifiers, processing aids, slip agents or anti-block agents. Processing aids include processing oils, which are well known in the art and include synthetic and natural oils, naphthenic oils, paraffinic oils, olefin oligomers and low molecular weight polymers, vegetable oils, animal oils, and derivatives of such including hydrogenated versions. Processing oils also may incorporate combinations of such oils. A particularly preferred processing oil is mineral oil. Viscosity modifiers are also well known in the art. For example, petroleum derived waxes can be used to reduce the viscosity of the slow recovery elastomer in thermal processing. Suitable waxes include low number-average molecular weight (e.g., 600-6000) polyethylene; petroleum waxes such as paraffin wax and microcrystalline wax; atactic polypropylene; synthetic waxes made by polymerizing carbon monoxide and hydrogen such as Fischer-Tropsch wax; and polyolefin waxes.

Various colorants and fillers are known in the art and may be included as additives within the composition that forms the elastic member 12. Colorants can include dyes and pigments such as titanium dioxide. Fillers may include such materials as talc and clay. Other additives may include dyes, UV absorbers, odor control agents, perfumes, fillers, desiccants, and the like.

Suitable substrates 14 for use include nonwoven webs, woven webs, knitted fabrics, films, film laminates, apertured films, nonwoven laminates, sponges, foams, scrims, and any combinations thereof. Suitable substrates may comprise natural materials, synthetic materials, or any combination thereof. For use in absorbent articles and particularly in diapers and like products, the substrate 14 is generally compliant, soft-feeling, and non-irritating to a wearer's skin. In certain embodiments, substrates 14 may include nonwoven webs such as spunbond webs, meltblown webs, carded webs, and combinations thereof (e.g., spunbond-meltblown composites and variants).

The dimensions of the substrate 14 are generally limited only by the requisite end-use of the slow recovery elastic laminate 10.

The SRSL 10 of the present invention exhibits unique elastic and recovery characteristics. The SRSL 10 exhibits a normalized unload force of greater than about 0.16 N/(g/m) at 37° C. as measured by the Two Cycle Hysteresis Test. Normalized unload forces of less than about 0.12 N/(g/m) at 37° C. are believed to be insufficient for use as an elastomer within absorbent articles. Laminates having normalized unload forces less than 0.12 N/(g/m) at 37° C. are unable to keep an absorbent article in snug, close contact to the wearer's skin. In certain embodiments, the SRSL 10 exhibits a normalized unload force of greater than about 0.24 N/(g/m) at 37° C.

Conventional stretch laminates (i.e., such as those commonly found in absorbent articles including diapers) exhibit minimal post elongation strain at 22° C. after 15 seconds of recovery. Qualitatively, conventional stretch laminates exhibit "snap back" (i.e., contracts relatively quickly after being released from a stretched state). In contrast, the SRSL 10 of the current invention exhibit a percent of initial strain of about 10% or greater after 15 seconds of recovery at 22° C., as measured by the Post Elongation Recovery Test. In other embodiments, the SRSL 10 exhibits a percent of initial strain of about 20% or greater after 15 seconds of recovery at 22° C. In other suitable embodiments, the SRSL 10 exhibits a percent of initial strain of about 30% or greater after 15 seconds of recovery at 22° C. In other suitable embodiments, the SRSL 10 exhibits a percent of initial strain of about 40% or greater after 15 seconds of recovery at 22° C.

Furthermore, the SRSL 10 of the present invention may exhibit a specified percent of initial strain at 22° C. after 30 seconds, 60 seconds, or three minutes of recovery. In certain embodiments, the SRSL 10 may exhibit a percent of initial strain at 22° C. after 30 seconds of recovery of about 10% or greater. Alternatively, the SRSL 10 may exhibit a percent of initial strain at 22° C. after 30 seconds of recovery about 15% or greater. In other embodiments, the SRSL 10 may exhibit a percent of initial strain at 22° C. after 60 seconds of recovery of about 10% or greater.

The SRSL 10 may exhibit temperature responsiveness. In certain embodiments, the SRSL 10 exhibits a percent of initial strain at 32° C. after a specified amount of recovery time that is less than the percent of initial strain exhibited at 22° C. after the same recovery time. In one embodiment, a temperature responsive SRSL 10 may exhibit a reduction in a percent of initial strain after 15 seconds at 32° C. as compared to the percent of initial strain exhibited after 15 seconds at 22° C. (i.e., [percent of initial strain after 15 seconds of recovery at 22° C.]–[percent of initial strain after 15 seconds of recovery at 32° C.]). In some embodiments, the difference is equal to or greater than 5%. In other embodiments, the SRSL 10 may exhibit a difference in the percent of initial strain after 15 seconds at 22° C. compared to after 15 seconds at 32° C. equal to or greater than 10%, 20%, 30%, or, alternatively, 40%. It is believed that a SRSL 10 exhibiting temperature responsiveness may further facilitate diaper application. When the diaper is applied at about room temperature (i.e., approximately 22° C.), the SRSL 10 may exhibit a relatively high percent of initial strain for a prescribed period of time, which allows the caregiver or wearer to apply the diaper. Upon application of the diaper, the temperature of the SRSL 10 will rise as a result of being in close proximity to the wearer's skin. As the temperature of the SRSL 10 increases and nears skin temperature (i.e., approximately 32° C.), the percent of initial strain is reduced. Temperature responsiveness allows for application of the diaper without "snap-back" while providing for increased recovery after application.

The SRSL 10 may be utilized in a variety of consumer and commercial products. However, the SRSL 10 has particular benefit within absorbent articles, particularly disposable absorbent articles such as diapers and the like. The SRSL 10 may be used in a variety of regions or in a variety of elements to provide elastic character to the absorbent article.

Figure 2:
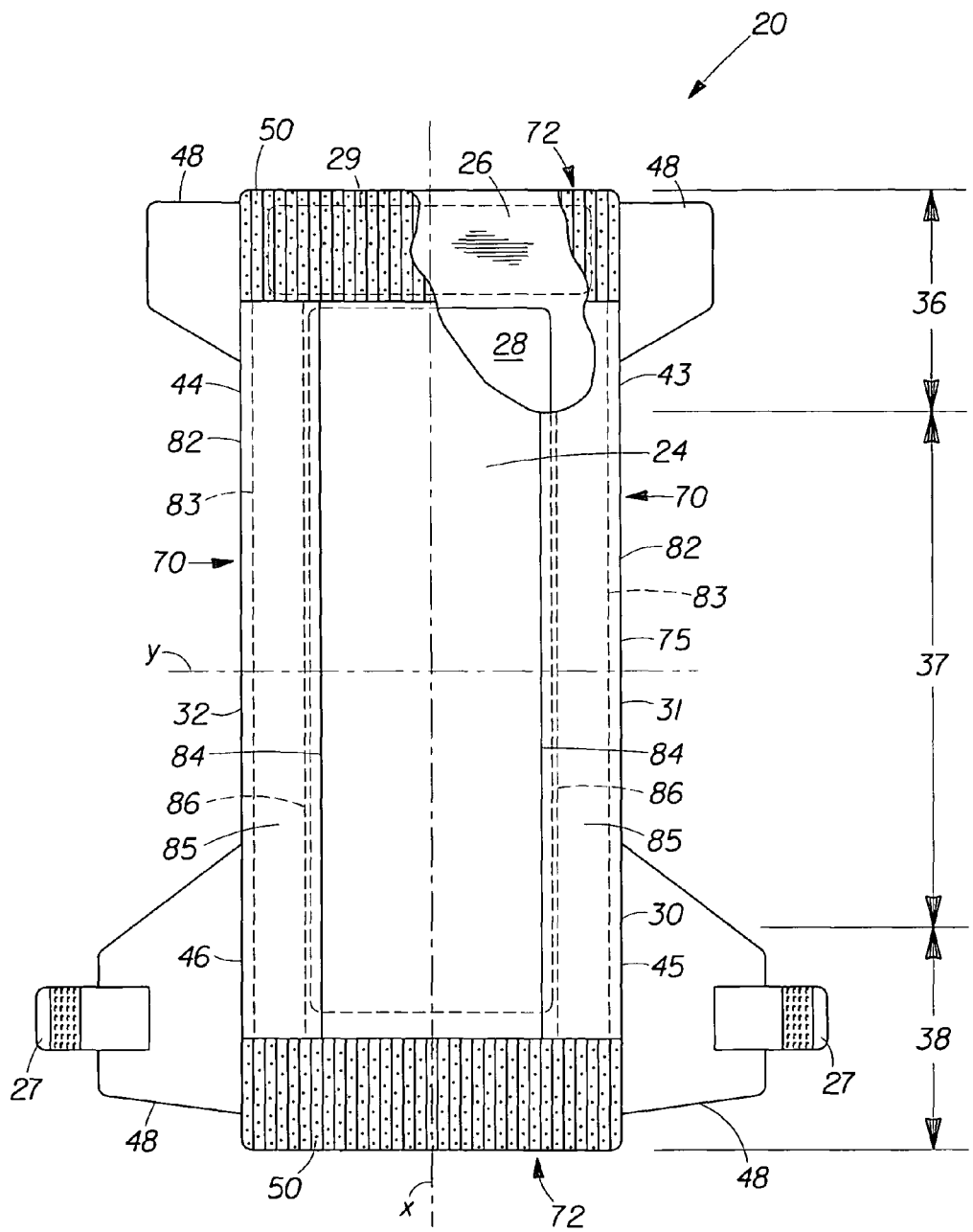
FIG. 2 is a top plan view of a diaper containing the slow recovery stretch laminate.

In the embodiment that follows, the absorbent article is in the form of a diaper 20. The SRSL of the present invention may be used in said embodiment wherever an elastic material is desired. It should be recognized that a diaper 20 may contain one or more SRSLs and one or more conventional stretch laminates. FIG. 2 illustrates a diaper 20 in a top plan view, stretched, and in a substantially planar state. The surface of the diaper 20 that is positioned proximate to the wearer (i.e., wearer-facing surface) is shown. Portions of the diaper 20 have been cut away to more clearly show the underlying structure. One end portion of the diaper 20 may be configured as a first waist region 36 of the diaper 20. The opposite end portion may be configured as a second waist region 38 of the diaper 20. An intermediate portion of the diaper 20 may be configured as a crotch region 37 that extends longitudinally between the first and second waist regions 36 and 38. The crotch region 37 is that portion of the diaper 20 which, when the diaper 20 is worn, is generally positioned between the legs of the wearer. The waist regions 36 and 38 generally may comprise those waist portions of the diaper 20 which, when worn, encircle the waist of the wearer. The waist regions 36 and 38 may include elements which can gather about the waist of the wearer to provide improved fit and containment, or which typically can gather around the waist and can be fastened around the waist by use of a fastening system, such as tabs 27, which may be fastened to a landing zone 29.

The diaper 20 may comprise two longitudinal edges 70 and two lateral edges 72. The diaper 20 may also have a longitudinal axis designated as line x. The diaper may also have a lateral axis designated as line y.

The diaper 20 may comprise at least one topsheet 24 that may be partially, fully, or not elasticated; a backsheet 26; and an absorbent core 28 interposed between the topsheet 24 and the backsheet 26. The diaper may also include side panels 48, a fastening system which may include fastening tabs 27 that can be secured to a landing zone 29, one or more pairs of leg cuffs 82, 84, and/or a waist feature 50.

The diaper 20 may comprise more than one topsheet. In FIG. 2, the diaper exhibits a single topsheet 24. The topsheet 24 may extend the width of the diaper 20 and may be positioned adjacent to the wearer-facing surface of the absorbent core 28. The topsheet 24 may be joined to the core 28 and/or to the backsheet 26 by any attachment means known in the art. Suitable attachment means for joining the topsheet 24 are the same as those means, as described below, for joining the backsheet 26 to other elements of the diaper 20. In one embodiment of the present invention, the topsheet 24 and the backsheet 26 are joined along their respective longitudinal edges 70 and lateral edges 72.

Suitable topsheets 24 may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If the topsheets include fibers, the fibers may be spunbond, carded, wet-laid, meltblown, hydroentangled, or otherwise processed as is known in the art. One suitable topsheet 24 is a web of hydrophilically treated spunbond polypropylene available from BBA Fiberweb, Old Hickory, Tenn., under the designation P10 or 055SLPI09E. Suitable formed film topsheets 24 are described in U.S. Pat. Nos. 3,929,135; 4,324,246; 4,342,314; 4,463,045; and 5,006,394. Other suitable topsheets 24 may be made in accordance with U.S. Pat. Nos. 4,609,518 and 4,629,643. Exemplary formed films include "DRI-WEAVE" and "CLIFF-T" both from Tredegar Corporation, Richmond, Va.

In certain embodiments, at least a portion of the topsheet 24 may comprise a hydrophobic material or may be treated to be hydrophobic in order to isolate the wearer's skin from liquids contained in the absorbent core 28. Hydrophobicity may be achieved by eliminating the hydrophilizing treatment step from the production process and/or applying a hydrophobic treatment to the topsheet 24, such as a fluoryl, paraffin, or silicone-based compound like Repellan ZN by Cognis Corporation, a hydrophobic surface coating as described in U.S. application Ser. No. 11/055,743, or a hydrophobic lotion composition, as described below. If the topsheet 24 is made of a hydrophobic material, it may be desirable that at least a portion of its surface is treated to be hydrophilic so that liquids will transfer through the topsheet more rapidly. The topsheet 24 can be rendered hydrophilic by treating it with a surfactant or by incorporating a surfactant into the topsheet. Suitable methods for treating the topsheet 24 with a surfactant include spraying the material with the surfactant and/or immersing the material into the surfactant. A more detailed discussion of such a treatment and hydrophilicity is contained in U.S. Pat. Nos. 4,988,344 and 4,988,345. A more detailed discussion of some suitable methods for incorporating a surfactant in the topsheet can be found in U.S. Statutory Invention Registration No. H1670 published on Jul. 1, 1997 to Aziz et al. Alternatively, the topsheet 24 may include an apertured web or film which is hydrophobic. In such embodiments, it is preferred that the apertures be large enough to allow the penetration of aqueous fluids like urine without significant resistance.

Any portion of the topsheet 24 may be coated with a lotion as is known in the art. Examples of suitable lotions include those described in U.S. Pat. Nos. 5,607,760; 5,609,587; 5,635,191; 5,643,588; and 5,968,025. The lotion may function alone or in combination with another agent such as the hydrophobizing treatment described above. The topsheet may also include or be treated with antibacterial agents, such as disclosed in U.S. Statutory Invention Registration No. H1732 published on Jun. 2, 1998 to Johnson. Further, the topsheet 24, the backsheet 26, or any portion of the topsheet or backsheet may be embossed and/or matte finished to provide a more cloth like appearance.

The backsheet 26 is generally that portion of the diaper 20 positioned adjacent to the garment facing surface of the absorbent core 28 which prevents the exudates absorbed and contained therein from soiling articles which may contact the diaper 20, such as bedsheets and undergarments. In certain embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Corporation, Richmond, Va., and sold under the trade name CPC2 film. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746; U.S. Pat. Nos. 5,938,648; 5,865,823; and 5,571,096.

The backsheet 26, or any portion thereof, may be elastically extensible in one or more directions. In one embodiment, the backsheet 26 may comprise a structural elastic-like film ("SELF") web as described in more detail in U.S. Pat. No. 5,518,801. In other embodiments, the backsheet 26 may comprise elastomeric films, foams, strands, or combinations of these or other suitable materials with nonwovens or synthetic films.

The backsheet 26 may be joined to the topsheet 24, the absorbent core 28 and/or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. Nos. 3,911,173; 4,785,996; and 4,842,666. Adhesives that have been found to be satisfactory are manufactured by H. B. Fuller Company, St. Paul, Minn., and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; and 5,625,222.

The diaper 20 may include a fastening system. The fastening system preferably maintains the first waist region 36 and the second waist region 38 in a configuration so as to provide lateral tensions about the circumference of the diaper 20 to hold the diaper 20 on the wearer. The fastening system typically includes at least one engaging component and at least one receiving component. An exemplary fastening system comprises fastening tabs 27 that may be secured to a landing zone 29. Other exemplary fastening systems include, but are not limited to, tape tabs, hook and loop fastening components, interlocking fasteners such as tabs and slots, buckles, buttons, snaps, adhesives, cohesives, and/or hermaphroditic fastening components, although other known fastening means are generally acceptable. Other exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098 entitled "Absorbent Article Fastening Device." The fastening system may also provide a means for holding the article in a disposal configuration as disclosed in U.S. Pat. No. 4,963,140. The fastening system may also include primary and secondary fastening systems, as disclosed in U.S. Pat. No. 4,699,622. The fastening system may also reduce shifting of overlapped portions or improve fit as disclosed in U.S. Pat. Nos. 5,242,436; 5,499,978; 5,507,736; and 5,591,152.

The diaper 20 may include one or more pairs of leg cuffs. Leg cuffs generally are generally disposed longitudinally on the diaper 20 and may be attached to the backsheet 26. FIG. 2 illustrates the diaper 20 as having two pairs of leg cuffs, a gasketing cuff 82 and a barrier cuff 84. U.S. Pat. Nos. 4,695,278 and 4,795,454 describe disposable diapers having leg cuffs in further detail. Gasketing cuffs 82 may also be referred to as outer leg cuffs, leg bands, side flaps, leg cuffs, or elastic cuffs. Barrier cuffs 84 may also be referred to as second cuffs, inner leg cuffs or "stand-up" elasticized flaps.

The gasketing cuff 82 may be substantially inelastic or may be elastically extensible to dynamically fit at the wearer's leg. The gasketing cuff 82 may be formed by one or more elastic members 83 operatively joined to the topsheet 24, backsheet 26, or any other suitable substrate used in the formation of the diaper 20. In one suitable embodiment, the gasketing cuff 82 has a plurality of elastic member 83 joined between the backsheet 26 and the topsheet 24. The elastic member 83 may be an elastic material that provides elasticity to the gasketing cuff 82 and may include the SRSL of the present invention.

The barrier cuff 84 may be formed by a flap 85 and an elastic member 86. The flap 85 may be a continuous extension of any of the existing materials or elements that form the diaper 20. For example, the flap 85 may be a portion of the topsheet 24 treated to be hydrophobic or the flap 85 may be a discrete element separately attached to diaper 20. The elastic member 86 may be an elastic material that provides elasticity to the barrier cuff 84 and may include the SRSL of the present invention. It is desirable that elastic member 86 exhibits sufficient elasticity such that the barrier cuff may remain in contact with the wearer during normal wear thus enhancing the barrier properties of the barrier cuff 84. U.S. Pat. Nos. 4,808,178 and 4,909,803 describe disposable diapers having barrier cuffs that improve the containment at the leg regions.

The leg cuffs 82, 84 may be treated, in full or in part, with a lotion, as described above. The leg cuffs may further be constructed in a number of different configurations, including those described in U.S. Pat. Nos. 4,636,207; 4,704,115; 4,900,317; 5,085,654; 5,492,751; 6,476,288; and SIR H1630. Any of the leg cuffs disclosed herein as well as other absorbent article components may also be fully or partially coated with a hydrophobic surface coating as detailed in U.S. application Ser. No. 11/055,743, which was filed Feb. 10, 2005.

The diaper 20 may also comprise side panels 48. The side panels 48 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 48 allow the sides of the diaper 20 to expand and contract. The side panels 48 may be disposed laterally from the longitudinal edge 70 of the diaper 20. Exemplary construction and configuration of side panels 48 are disclosed in U.S. Pat. Nos. 3,860,003; 4,857,067; 4,381,781; 4,938,753; 5,151,092; 5,221,274; 5,669,897; and 6,004,306. Particularly for traditional taped-type diapers, such as the one shown in FIG. 2, the side panels 48 are also known in the art as ears. The ears disposed in the first waist region 36 may be designated front ears and the ears disposed in the second waist region 38 may be designated back ears.

The diaper 20 may also comprise an elastic waist feature 50. The elastic waist feature 50 is generally intended to elastically expand and contract to dynamically fit the wearer's waist. The waist feature 50 may enable the diaper 20 to provide improved fit and containment. The diaper may have two elastic waist features 50, one positioned in the first waist region 36 and one positioned in the second waist region 38. The elastic waist feature 50 may be joined to the wearer-facing surface of the diaper 20. The elastic waist feature 50 may be joined to the topsheet 24. The elastic waist feature 50 may be constructed in a number of different configurations including those described in U.S. Pat. Nos. 4,515,595; 4,710,189; 5,151,092; and 5,221,274. Other suitable waist configurations may include waistcap features such as those described in U.S. Pat. Nos. 5,026,364 and 4,816,025. Elasticity may be provided to the elastic waist feature by inclusion of the SRSL of the present invention.

Some embodiments may also include pockets for receiving and containing waste, spacers which provide voids for waste, barriers for limiting the movement of waste in the article, compartments or voids which accept and contain waste materials deposited in the diaper 20, and the like, or any combinations thereof. Examples of pockets and spacers for use in absorbent products are described in U.S. Pat. Nos. 5,514,121; 5,171,236; 5,397,318; 5,540,671; 6,168,584; 5,306,266; and 5,997,520. Examples of compartments or voids are disclosed in U.S. Pat. Nos. 4,968,312; 4,990,147; 5,062,840; and 5,269,755. Examples of suitable transverse barriers are described in U.S. Pat. No. 5,554,142; WO 94/14395; and U.S. Pat. No. 5,653,703. Examples of other structures especially suitable for management of low viscosity feces are disclosed in U.S. Pat. Nos. 5,941,864; 5,977,430; and 6,013,063.

Other suitable embodiments for incorporation of SRSL into absorbent articles include using SRSLs to form stretch zones as disclosed in co-pending U.S. application Ser. No. 11/145,353 filed on Jun. 3, 2005 in the name of McKiernan et al., which claims the benefit of U.S. Provisional Application No. 60/643,920, filed Jan. 10, 2005.

Figure 3A:
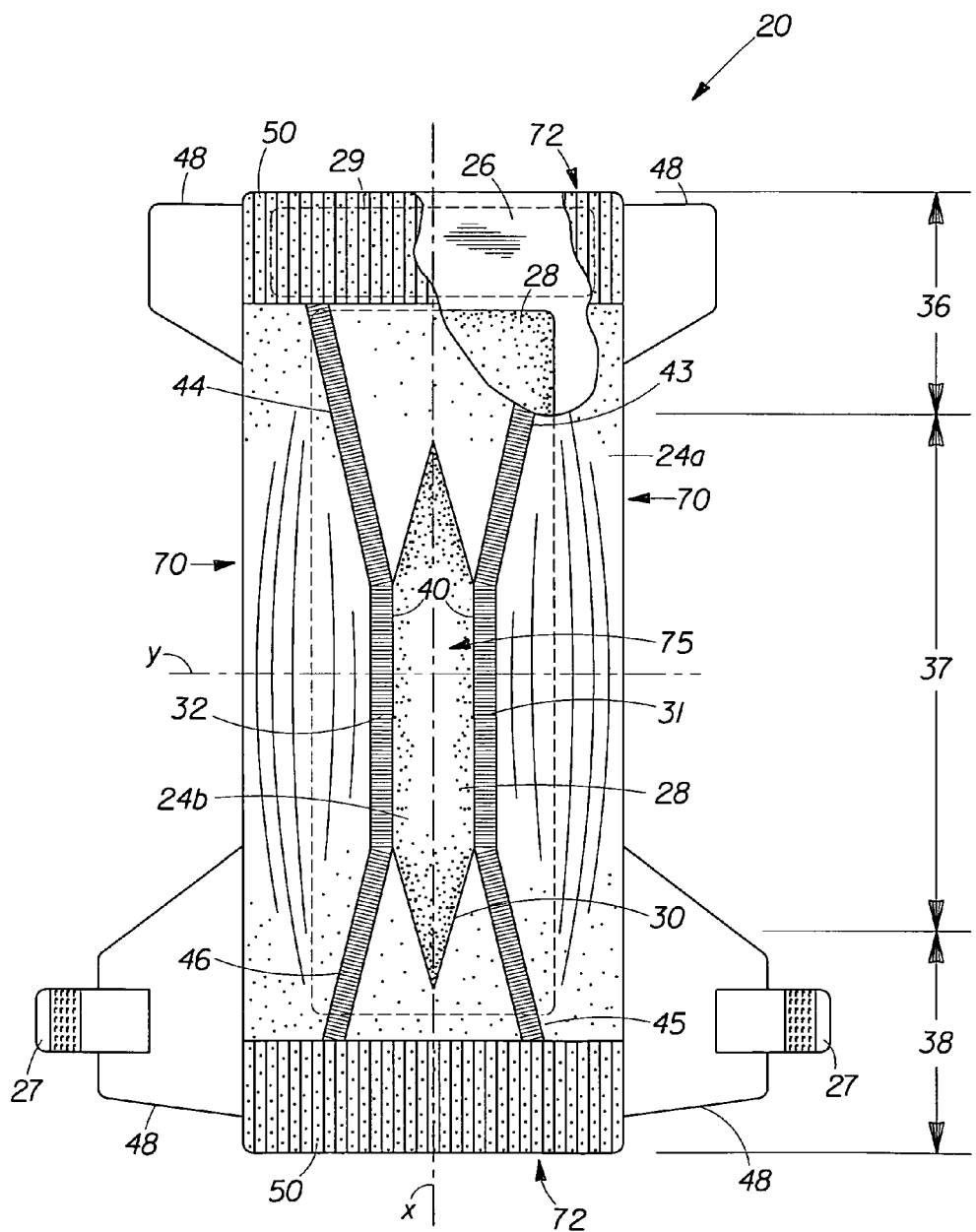
FIG. 3A is a top plan view of another embodiment of a diaper containing the slow recovery stretch laminate.

FIG. 3A illustrates a diaper 20 in a top plan view, stretched, and in a substantially planar state. The surface of the diaper 20 that is positioned proximate to the wearer (i.e., wearer-facing surface) is shown. Portions of the diaper 20 have been cut away to more clearly show the underlying structure. In this embodiment, the diaper exhibits two topsheets, an elasticized topsheet 24a and a secondary topsheet 24b. The secondary topsheet 24b may extend the width of the diaper 20 and may be positioned adjacent to the wearer-facing surface of the absorbent core 28. The secondary topsheet 24b may be used so that fecal insult will not adversely associate with the absorbent core 28. Generally in a diaper comprising two topsheets, the secondary topsheet 24b is the topsheet proximate to the garment-facing surface of the diaper 20 whereas the elasticized topsheet 24a is proximate to the wearer-facing surface. The secondary topsheet 24b may be joined to the core 28 and/or to the backsheet 26 by any attachment means known in the art. Suitable attachment means for joining the topsheets 24a and 24b are the same as those means, as described below, for joining the backsheet 26 to other elements of the diaper 20. In one embodiment of the present invention, the topsheets 24a and 24b and the backsheet 26 are joined along their respective longitudinal edge 70 and lateral edges 72. The elasticized topsheet 24a and the secondary topsheet 24b may be joined along one or more of their longitudinal edges 70 or lateral edges 72 and not along a substantial portion of their contacting planar faces. In certain embodiments, the secondary topsheet 24b is not attached to the core 28.

The secondary topsheet 24b may be liquid pervious, permitting liquids to readily penetrate through its thickness. The elasticized topsheet 24a may be hydrophobic in order to isolate liquids contained in the absorbent core 28 from the wearer's skin.

The topsheets 24a and 24b may be manufactured from a wide range of materials as described above in regard to topsheet 24. In certain embodiments, as described above in regard to topsheet 24, a portion of the secondary topsheet 24b and/or the elasticized topsheet 24a may comprise a hydrophobic material or may be treated to be hydrophobic in order to isolate the wearer's skin from liquids contained in the absorbent core 28. If necessary, the topsheets 24a and 24b may comprise a hydrophilic material or may be rendered hydrophilic as described above in regard to the topsheet 24. Topsheets 24a and 24b may be coated with a lotion as is known in the art as described above in reference to topsheet 24. Furthermore, the topsheets 24a and 24b and the backsheet 26 may be fully or partially embossed and/or matte finished to provide a more cloth like appearance.

The diaper 20 may comprise a slit opening 30 through the elasticized topsheet 24a. The slit opening 30 may be located so that fecal exudates pass through the slit opening 30 and into a void space 75 formed between the elasticized topsheet 24a and the secondary topsheet 24b. In other embodiments without a secondary topsheet 24b, the void space 75 may be formed between the elasticized topsheet 24a and the absorbent core 28 and/or other underlying layers such as sub layers, acquisition layers and the like. The void space 75 entraps or encapsulates bodily waste. It is also contemplated that the void space 75 may be formed between two elements of the diaper 20, including but not limited to a topsheet (either a conventional or elasticized topsheet) and the backsheet 26, the acquisition layer and the core 28, the core 28 and the backsheet 26, etc.

The slit opening 30 may be shaped to allow passage of bodily waste. An example of a suitably shaped slit opening 30 is a hexagonal shaped slit opening 30 as shown in FIG. 3A. However, it will be apparent to one of skill in the art that other shapes and sizes of the slit opening 30 are feasible.

The elasticized topsheet 24a may comprise an elastic structure 31, 32. The elastic structure 31, 32 may be located along at least a portion of the longitudinal edges 40 of the slit opening 30. The longitudinal edge 40 of the slit opening may be held against the wearer's skin allowing the feces to penetrate the slit opening 30 without deflection, via only the elastic forces supplied by the elastic structure 31, 32, or optionally by use of a body adhering adhesive. The elastic structure 31, 32 may assist in maintaining the elasticized topsheet 24a in close contact to the wearer's skin. The elastic structure 31, 32 also may assist in maintaining the position of the slit opening 30 along a gluteal groove, including a perianal region.

The elastic structure 31, 32 may be the SRSL of the present invention. The elastic structure 31, 32 may comprise other traditional "fast" elastic materials including synthetic rubber such as supplied by Fulflex International, Ireland; polyurethane such as Lycra® available from Invista Inc., Wilmington, Del.; or a VFE material available from Tredegar Corporation, Richmond, Va. The SRSL may be bonded to the elasticized topsheet 24a by any method well known in the art including heat bonding and the use of adhesives (e.g., HL-1620 available by H. B. Fuller Company of St. Paul, Minn.). The elastic structure 31, 32 may be positioned along the longitudinal edges 40 of the slit opening 30. The elastic structure 31, 32 may extend from the slit opening 30 in the direction of the waist regions, preferably in an X-shape, with a front stretch laminate 43, 44 and/or a back stretch laminate 45, 46. The stretch laminate may be attached to a waistband, if present.

Figure 3B:
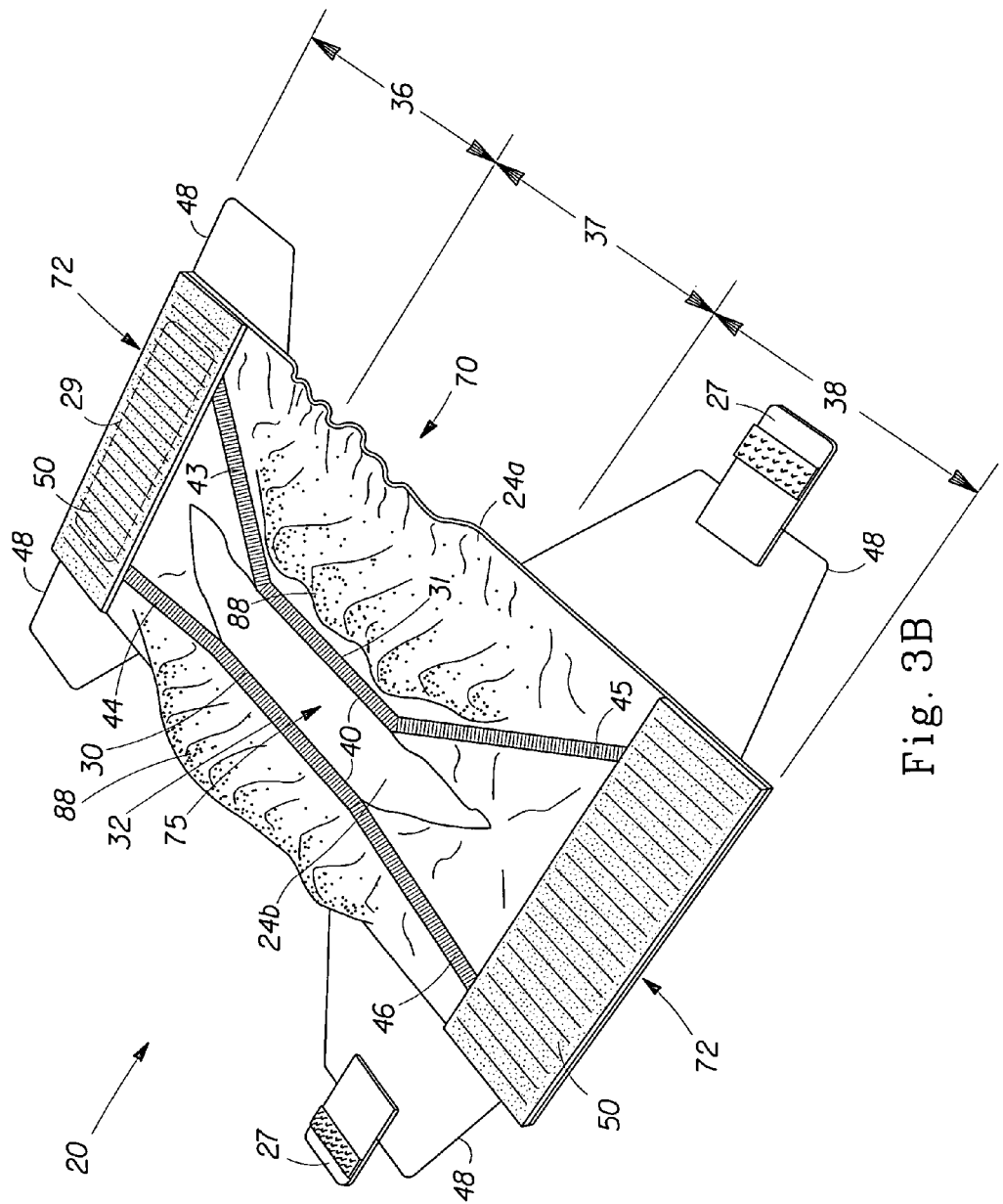
FIG. 3B is a perspective view of the diaper, as shown in FIG. 3A, containing the slow recovery stretch laminate.

FIG. 3B shows a perspective view of the diaper 20 of FIG. 3A. The elasticized topsheet 24a may comprise folds 88 which unfold when a low force, such as less than about 1 N, is applied to the elasticized topsheet 24a. The folds 88 may allow the elasticized topsheet 24a to extend during wear. For example, when the secondary topsheet 24b, backsheet 26, and core 28 become heavier upon receipt of bodily exudates and start to sag downwards, the folds 88 can straighten thus allowing the elasticized topsheet 24 to extend and remain positioned in close proximity to the wearer's skin. Also, with limited or no attachment of the elasticized topsheet 24a to the core 28, when the core 28 and backsheet 26 are pulled downwards due to the weight of the exudates received by the diaper 20, the elasticized topsheet 24a and the slit opening 30 do not move automatically with the core but remain against the skin of the wearer, or in very close proximity to the wearer. It is believed that, by minimizing or preventing movement, the slit opening 30 will not increase significantly in lateral size; thus, minimizing potential skin contact with fecal matter.

Figure 4A:
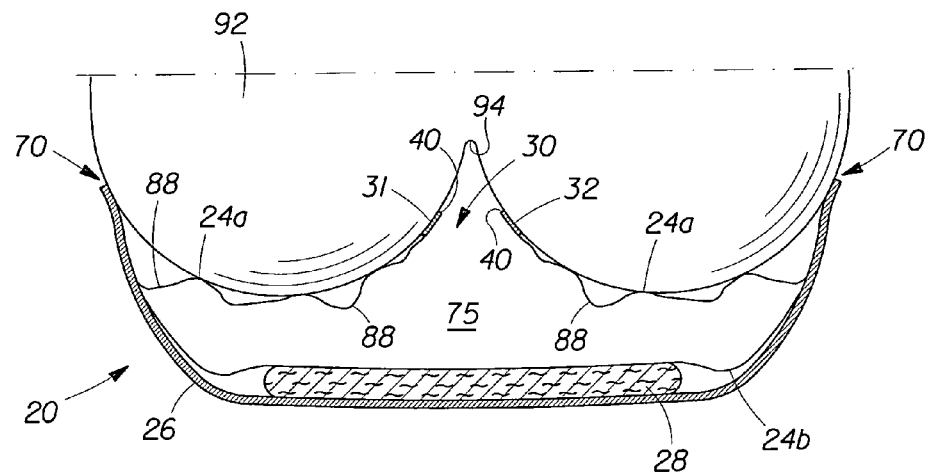
FIGS. 4A and 4B are cross-sectional views of the diaper, as shown in FIG. 3A, while in use before and after being soiled.
Figure 4B:
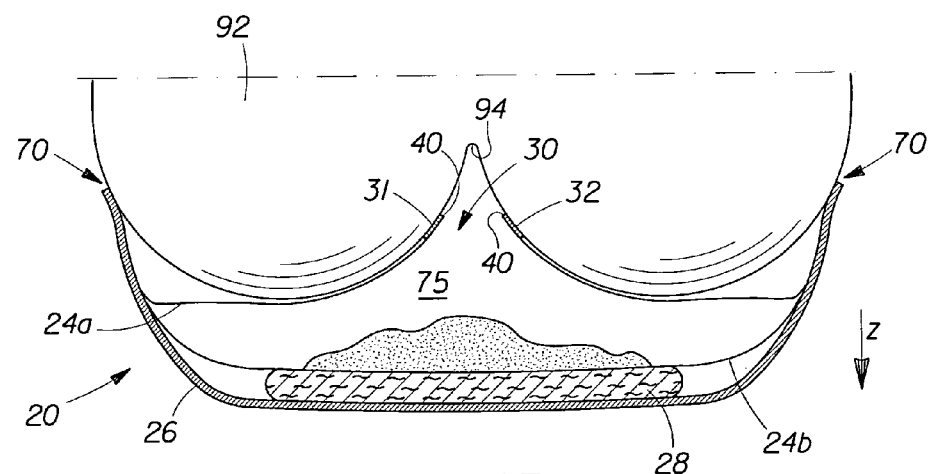

FIGS. 4A-B are cross-sectional views of the diaper 20 taken along a sectional line designated y (i.e., the lateral axis) of FIG. 3A. The diaper 20 is being worn by a wearer 92 such that the elasticized topsheet 24a and elastic structure 31, 32 are in close proximity to the wearer 92. The longitudinal edges 40 are positioned such that the slit opening 30 is positioned along a gluteal groove 94 so as to receive fecal insult. The position of the longitudinal edges 40 and the slit opening 30 may be positioned with respect to the gluteal groove 94 so as to prevent fecal insult on the elasticized topsheet 24a. FIG. 4A shows the diaper prior to receiving exudates. In FIG. 4B, the diaper 20 has received bodily exudates 96. The exudates 96 have passed through the slit opening 30, into the void space 75, and are deposited on the secondary topsheet 24b. The secondary topsheet 24b, core 28, and backsheet 26 now having this increased load may move downward in the z direction (i.e., exhibit sagging). However, the elastic structure 31, 32 and the slit opening 30 have not moved substantially from the original position shown in FIG. 4A. The folds present in the elasticized topsheet 24a unfurl (i.e., straighten out or unfold) and compensate for the extension of the backsheet 26, core 28, and secondary topsheet 24b in the downward direction.

In other embodiments, the elasticized topsheet 24a and the secondary topsheet 24b may both comprise the stretch laminate of the present invention. In other embodiments, the diaper 20 may take a variety of other forms and constructions as exemplified in U.S. patent application Ser. No. 10/764,939 (U.S. Publication No. U.S. 2004/0193134 A1); U.S. Pat. No. 6,482,191; U.S. patent application Ser. No. 10/764,850 (U.S. Publication No. U.S. 2004/0162538 A1); U.S. patent application Ser. No. 10/703,239 (U.S. Publication No. U.S. 2004/0092902 A1); and U.S. patent application Ser. No. 10/703,233 (U.S. Publication No. U.S. 2004/0092900 A1). The SRSL of the present invention may be substituted for the elastic regions, bands, or member as disclosed in the referenced application.

Figure 5A:
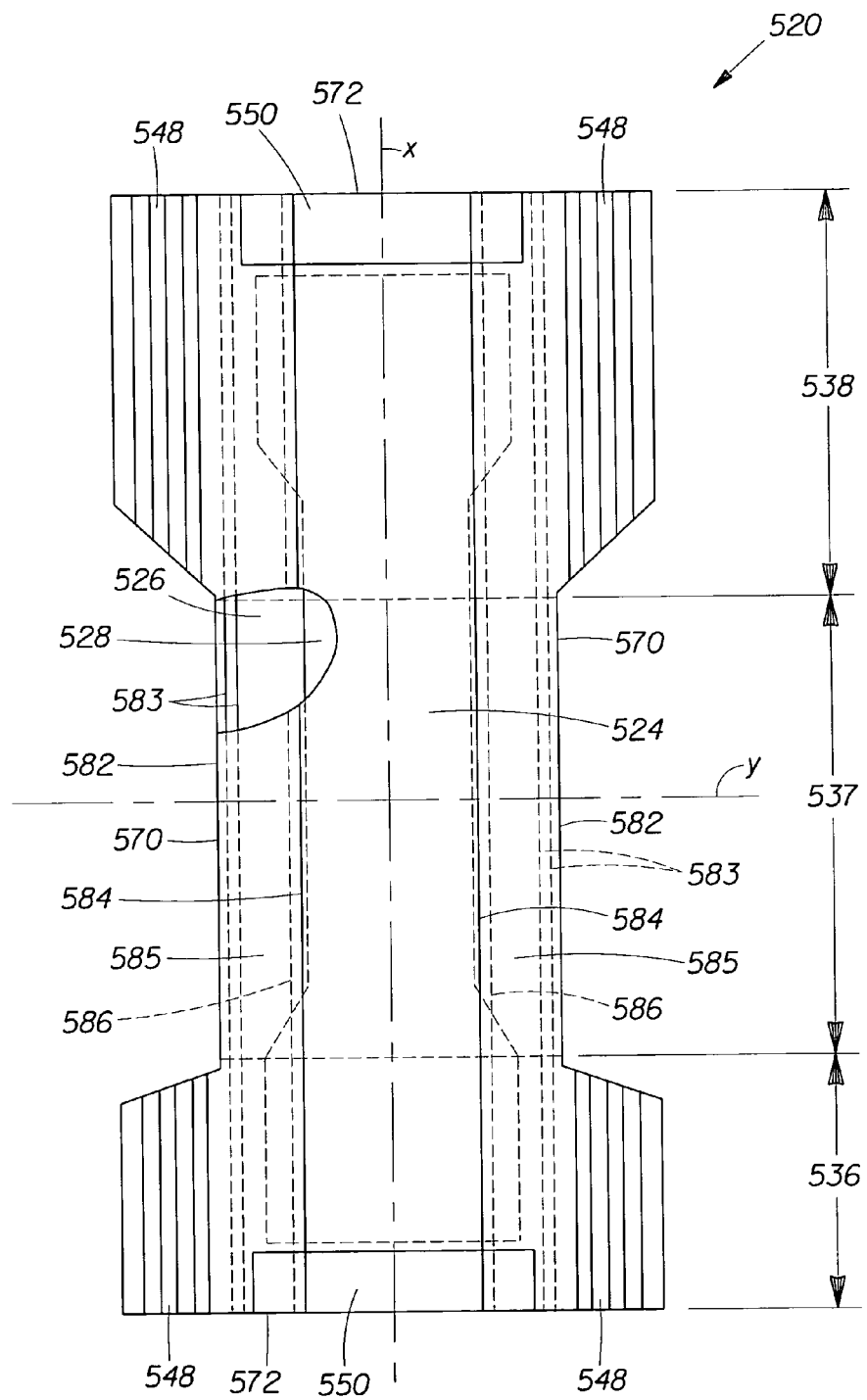
FIG. 5A is a top plan view of another embodiment of the absorbent article as a pant in an unseamed state.
Figure 5B:
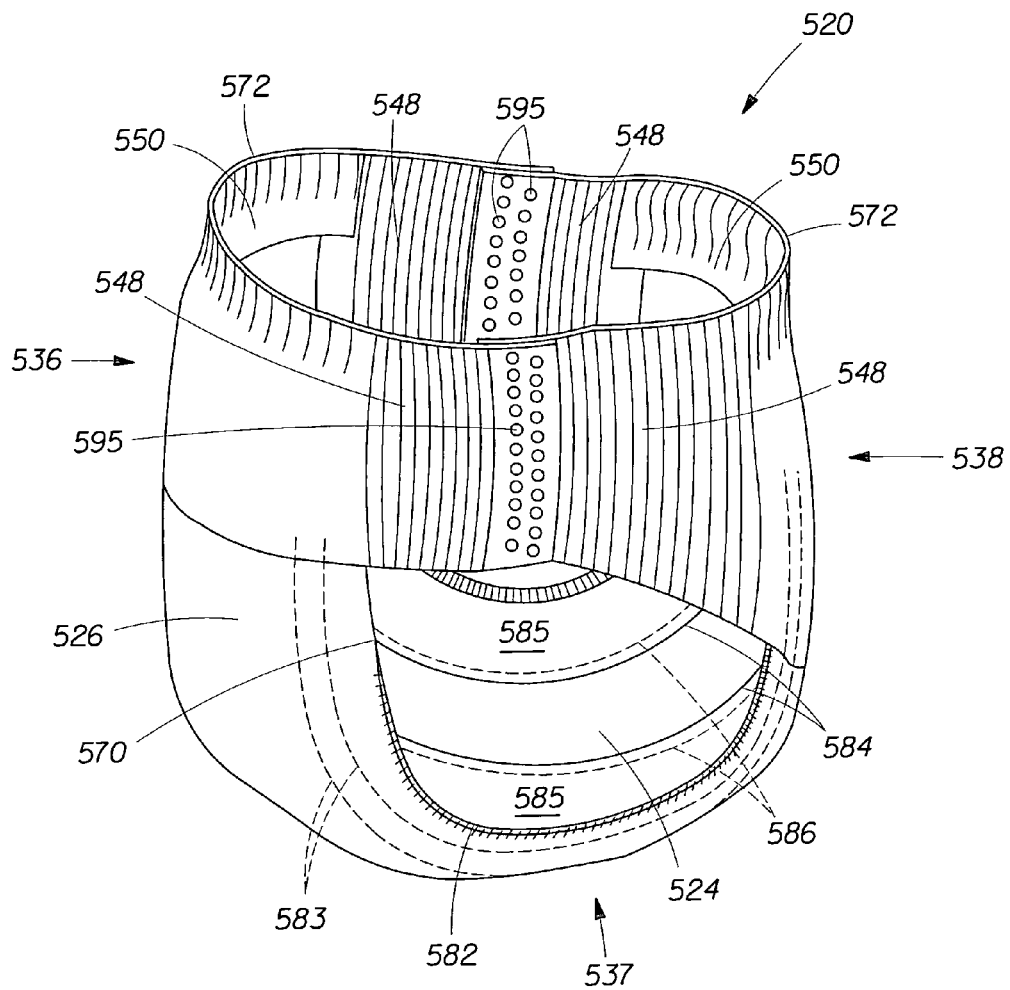
FIG. 5B is a perspective view of the pant of FIG. 5A shown in a seamed state.

In alternative embodiments, the diaper may be pre-formed by the manufacturer to create a pant. Pant generically refers to disposable garments having a waist opening and leg openings designed for infant or adult wearers. Pants are also commonly referred to as "closed diapers," "prefastened diapers," "pull-on diapers," "training pants," and "diaper-pants." The pant may be placed in position on the wearer by inserting the wearer's legs into the leg openings and sliding the pant into position about the wearer's lower torso. An exemplary pant 520 is shown in FIGS. 5A-B. The pant 520 is in a planar unseamed state in FIG. 5a with the wearer-facing surface facing the viewer and is shown seamed in the perspective view of FIG. 5b. The pant 520 may comprise many of the same elements as the diapers of FIGS. 2-4. One end portion of the pant 520 may be configured as a first waist region 536. The opposite end portion may be configured as a second waist region 538. An intermediate portion of the pant 520 may be configured as a crotch-region 537 that extends longitudinally between the first and second waist regions 536 and 538.

The pant 520 may comprise two longitudinal edges 570 and two lateral edges 572. The pant 520 may also have a longitudinal axis designated as line x. The pant 520 may also have a lateral axis designated as line y. The pant 520 may comprise at least one topsheet 524 that may be partially, fully, or not elasticated; a backsheet 526; and an absorbent core 528 interposed between the topsheet 524 and the backsheet 526. The pant 520 may also include side panels 548; one or more pairs of leg cuffs such as gasketing cuffs 582 which may have an elastic member 583 and barrier cuffs 584 which may have a flap 585 and an elastic member 586; and/or a waist feature 550. It should be recognized that the pant 520 may be configured with a single topsheet 24 as depicted in diaper 20 in FIG. 2, or the pant 520 may be configured with more than one topsheet, such as the elasticized topsheet 24a and secondary topsheet 24b as depicted in diaper 20 in FIGS. 3-4.

The pant may be pre-formed such that the first waist region 536 is joined to the second waist region 538 thereby forming a waist opening and a pair of leg openings. The pant 520 may be pre-formed by having opposing side panels 548 in the first waist region 536 joined to the opposing side panels 548 in the second waist region 538 by a seam 595, as shown in FIG. 5b. The seam 595 may be formed by any suitable bonding means known in the art which is appropriate for the specific materials employed. For example, suitable bonding means may include ultrasonic sealing, heat sealing, pressure bonding, adhesive bonding, sewing, autogenous bonding, and the like. The seams 595 may be permanent, that is, they may be bonded such that separation of the joined opposing side edges 548 requires the rupture or other destructive manipulation of the bonded materials that prevents refastening of the side edges 548. Alternatively, the seam 595 may be refastenable such that it can be opened and refastened repeatedly. Refastenable seams may include hook and loop fasteners and the like. Suitable pants are disclosed in U.S. Pat. Nos. 5,246,433; 5,569,234; 6,120,487; 6,120,489; 4,940,464; 5,092,861; 5,897,545; 5,957,908; and U.S. patent application Ser. No. 10/171,249.

Another embodiment of the present invention is directed toward a method of applying any of the absorbent articles as disclosed above. The absorbent article may be provided to a caregiver for application onto a wearer. The absorbent article may be in a compacted state such that a stretch laminate comprising a SRSL is in a relaxed, substantially untensioned state. The caregiver may stretch the absorbent article thereby expanding and tensioning the stretch laminate. The article is generally stretched in preparation for application. The absorbent article can maintain a functionally elongated state for an effective period of time. In one embodiment, the article may maintain an elongated state for a sufficient amount of time necessary for the caregiver to apply the article to the wearer. Upon release of the diaper after stretching, the diaper often contracts and/or folds before it can be successfully applied to a wearer. In one embodiment, SRSL exhibits a percent of initial strain after 15 seconds of recovery at 22° C. of greater than or equal to 10%. After application, the article may continue to contract so as to provide a snug, ideal fit. This method may be repeated upon soiling of the article during wear.

In another embodiment, a plurality of absorbent articles as disclosed above may be packaged in a kit. Generally, the kit allows for a quantity of absorbent articles to be delivered to and purchased by a consumer while economizing space and simplifying transport and storage. The kit may require activation so that the article becomes accessible (e.g., opening of a lid, removal of a panel, etc.). In one embodiment, the kit is defined by numerous absorbent articles bound together as an entity and covered by a thermoplastic film overwrap as disclosed in U.S. Pat. No. 5,934,470. The thermoplastic film cover may contain an opening means to allow removal of a portion of the thermoplastic film cover and access to the articles. A typical opening means may include a substantially continuous line of weakness, preferably perforations within the thermoplastic film cover. An exemplary opening means is presented in U.S. Pat. No. 5,036,978.

While one kit embodiment is described above, other variations to the kit are clearly envisioned. The overwrap may comprise a variety of materials including, but not limited to, thermoplastic films, nonwovens, wovens, foils, fabrics, papers, cardboard, elastics, cords, straps, and combinations thereof. The overwrap may completely or partially bind and/or cover the plurality of pull-on garments. Other particularly preferred packages and methods for packaging are disclosed in U.S. Pat. Nos. 5,050,742 and 5,054,619. Furthermore, a kit may contain multiple overwraps. For example, a plurality of pull-on garments of the present inventions may be packaged with a thermoplastic film overwrap and then a plurality of film wrapped pull-on garments being overwrapped in a cardboard box or a second thermoplastic film overwrap. Furthermore, the kit may not contain a dedicated opening means. For example, a thermoplastic film overwrap without perforation may simply be opened by tearing the film.

Test Methods

Post Elongation Recovery

This method is used to determine the post elongation strain of a stretch laminate as a function of temperature and time. The measurement is done at 22° C. (72° F.) or at 32° C. (90° F.). The measurement at 22° C. (72° F.) is designed to simulate the recovery of the stretch laminate at room temperature, while the measurement at 32° C. (90° F.) is designed to measure the recovery of the stretch laminate near skin temperature. A two-step analysis, Stretch and Recovery, is performed on the samples. The method employs a Dynamic Mechanical Analyzer. A TA Instruments DMA 2980 (hereinafter "DMA 2980"), available from TA Instruments, Inc., of New Castle, Del.; equipped with a film clamp, Thermal Advantage/Thermal Solutions software for data acquisition, and Universal Analysis 2000 software for data analysis was used herein. Many other types of DMA devices exist, and the use of dynamic mechanical analysis is well known to those skilled in the art of polymer and copolymer characterization.

Methods of operation, calibration and guidelines for using the DMA 2980 are found in TA Instruments DMA 2980 Operator's Manual issued March 2002, Thermal Advantage User's Reference Guide issued July 2000 and Universal Analysis 2000 guide issued February 2003. To those skilled in the use of the DMA 2980, the following operational run conditions should be sufficient to replicate the stretch and recovery of the samples.

The DMA 2980 was configured to operate in the Controlled Force Mode with the film clamp. The film clamp is mounted onto the DMA 2980 and calibrated according to the User's Reference Guide. The stretch laminate to be tested is cut into samples of substantially uniform dimension. For the DMA 2980, suitable sample dimensions are approximately 20 mm×6.4 mm×1.0 mm (length×width×thickness). The sample thickness is dependent on the materials and structure of the stretch laminate and on the confining pressure used to measure the thickness. TA Instruments recommends the sample thickness, when securely mounted within the film clamps, to be less than or equal to about 2.0 mm. The lower film clamp of the DMA 2980 is adjusted and locked in a position which provides approximately 10 mm between the clamping surfaces. The sample is mounted in the film clamps and the lower clamp is allowed to float to determine the gauge length between the film clamps. The sample ID and dimensions are recorded. The film clamp is locked in position and the furnace is closed.

Stretch Method—For the sample dimensions specified above, the DMA 2980 is configured as follows: Preload force applied to sample in clamp (0.01 N); auto zero displacement (on) at the start of the test; furnace (close), clamp position (lock), and temperature held at $T_i$ (22° C. or 32° C.) at the end of the stretch method. Data acquisition rate is set at 0.5 Hz (1 point per 2 seconds). The stretch method is loaded onto the DMA 2980. The method segments are (1) Initial Temperature $T_i$ (22° C. or 32° C.), (2) Equilibrate at $T_i$ (3) Data Storage ON, and (4) Ramp Force 5.0 N/min to 18.0 N.

Upon initiation of the test, the temperature ramps to the specified $T_i$ (22° C. or 32° C.) [method segment 1], and the temperature is maintained at this $T_i$ [method segment 2]. After a minimum of 15 minutes at $T_i$, the operator initiates the sample stretching and concurrent data collection [method segments 3 and 4]. The sample is stretched with an applied ramp force of 0.8 N/min per millimeter of initial sample width (e.g., for the sample dimensions specified above, the applied ramp force is 5 N/minute) to approximately 30 mm in length. The gradual increase in force more closely simulates application of the article and prevents sample breakage. The sample is locked in place at the stretched length of approximately 30 mm and maintained at $T_i$. The force required to stretch the laminate to a length of approximately 30 mm and the percent strain of the laminate at this length are recorded manually from the digital readout on the instrument. The percent strain is calculated by subtracting the gauge length from the stretched length, then dividing the result by the gauge length and multiplying by 100. The initial percent strain is described by the equation below:

$$\text{Initial Percent Strain} = \% \text{ Strain}_i = 100 * ((Ls - L_g)/L_g)$$

where $L_g$ is the length of the gathered stretch laminate in a relaxed state and Ls is the length of the stretched laminate between the film clamps at the end of the stretch step of the analysis (~30 mm). % $\text{Strain}_i$ is the percent strain of the stretch laminate at the start of the recovery method (i.e. after the stretch part of the method is complete). A sample stretched from a gauge length of 10 mm to a length of 30 mm results in a percent strain of 200%.

Stretch laminates may be unable to exhibit extensibility of 200% strain without incurring irreversible deformation, delamination, or tearing. This is particularly true for stretch laminates obtained from commercially available products such as the side panels, leg cuffs and waistbands of diapers. For example, a stretch laminate (~6.4 mm wide) may be easily stretched to 100% strain or 150% strain when relatively low forces (<4 N) are applied. However, if the applied force continues to increase to achieve 200% strain, the percent strain of the stretch laminate plateaus and further extension may be difficult and/or may result in irreversible deformation, delamination, or tearing of the stretch laminate. For purposes of this test, the maximum percent strain (e.g., 200%, 150%, or 100%) is to be chosen such that the strain does not result in irreversible deformation, delamination, or tearing of the stretch laminate. If the stretch laminate has an extensibility of less than 200% strain (±5%), a new specimen of the sample is stretched from a gauge length of 12 mm to an extended length of 30 mm which results in a percent strain of 150%. If the stretch laminate has an extensibility of less than 150% strain (±5%), a new specimen of the sample is stretched from a gauge length of 15 mm to an extended length of 30 mm which results in a percent strain of 100% strain. Testing of stretch laminates with maximum extensibility of <100% is also within the scope of this method. For stretch laminates tested at an initial percent strain of 100% or less, the post elongation strain is reported as the percent strain rather than the percent of initial % strain at the different times of recovery (15 seconds, 30 seconds, 60 seconds and 3 minutes).

For samples of different dimensions, the applied force to stretch the sample is adjusted to achieve an applied ramp force of 0.8 N/min per millimeter of initial sample width. For example, a force ramp of 2.5 N/min is applied to a sample with an initial width of 3.2 mm. For samples of different lengths, the total displacement during the elongation is adjusted to achieve an initial percent strain of 200% (or less if the sample has limited extensibility, i.e. 150% or 100% strain).

Recovery Method—The Recovery Method is loaded onto the instrument and initiated approximately 15 seconds after reaching the desired initial percent strain (i.e. 200%, 150%, or 100%) in the Stretch Method. The four segments of the recovery method are (1) Data Storage ON, (2) Force 0.01 N, (3) Ramp to $T_i$, and (4) Isotherm for 3.0 minutes. The following DMA 2980 parameter setting is changed from the Stretch Method: auto zero displacement is changed to (OFF). The Recovery Method measures the length of the sample over a 3 minute time period at the specified temperature ($T_i$=either 22° C. or 32° C.). The sample length, percent strain, and test temperature are recorded as a function of recovery time. The post elongation strain is reported as the percent of the initial percent strain after different times of recovery (15 seconds, 30 seconds, 60 seconds, and 3 minutes).

For samples of different dimensions, the force applied to the sample during recovery (segment 2 above) is adjusted to achieve an applied force of 0.0016 N per millimeter of initial sample width (0.01 N for 6.4 mm wide sample). For example, a force of 0.005 N is applied to a sample 3.2 mm wide.

Two Cycle Hysteresis Test

This method is used to determine properties that may correlate with the forces experienced by the consumer during application of the product containing the slow recovery stretch laminate and how the product fits and performs once it is applied.

The two cycle hysteresis test method is performed at room temperature (21° C./70° F.) and also at body temperature (37° C./99° F.). The stretch laminate to be tested is cut into a sample of substantially rectilinear dimensions. Sample dimensions are selected to achieve the required strain with forces appropriate for the instrument. Suitable instruments for this test include tensile testers commercially available from MTS Systems Corp., Eden Prairie, Minn. (e.g. Alliance RT/1 or Sintech 1/S) or from Instron Engineering Corp., Canton, Mass. For either the Alliance RT/1 or Sintech 1/S instruments listed above, suitable sample dimensions are approximately 25 mm wide by approximately 100 mm long. The sample thickness is dependent on the materials and structure of the stretch laminate and on the confining pressure used to measure the thickness. The thicknesses of samples are typically 0.5 mm to 5 mm thick measured with 0.2 psi confining pressure. However, testing of stretch laminates with different thicknesses (e.g., <0.5 mm or >5 mm) is within the scope of this method.

The following procedure illustrates the measurement when using the above sample dimensions and either an Alliance RT/1 or Sintech 1/S. The instrument is interfaced with a computer. TestWorks 4™ software controls the testing parameters, performs data acquisition and calculation, and provides graphs and data reports.

The widths of the grips used for the test are greater than or equal to the width of the sample. Typically 1" (2.54 cm) wide grips are used. The grips are air actuated grips designed to concentrate the entire gripping force along a single line perpendicular to the direction of testing stress having one flat surface and an opposing face from which protrudes a half round (radius=6 mm) to minimize slippage of the sample. In the case of the measurement at 37° C., the upper grip is a lightweight grip with serrated faces.

The load cell is selected so that the forces measured will be between 10% and 90% of the capacity of the load cell or the load range used. Typically a 25 N load cell is used. The fixtures and grips are installed. The instrument is calibrated according to the manufacturer's instructions. The distance between the lines of gripping force (gauge length) is 2.50" (63.5 mm), which is measured with a steel ruler held beside the grips. The load reading on the instrument is zeroed to account for the mass of the fixture and grips. The specimen is equilibrated a minimum of 1 hour at 21° C. before testing. The specimen is mounted into the grips in a manner such that there is no slack and the load measured is between 0.00 N and 0.02 N. The instrument is located in a temperature-controlled room for measurements performed at 21° C. A suitable environmental chamber is used to maintain the testing temperature for measurements performed at 37° C.; the sample is mounted in the grips and equilibrated for 5 minutes at 37° C. before starting the test.

The 2 cycle hysteresis test method involves the following steps:
(1) Strain the sample to the specified initial percent strain (i.e., $Strain_i=150\%$) at a constant crosshead speed of 20"/min. (50.8 cm/min) with no hold.
(2) Reduce the strain to 0% strain (i.e., return grips to the original gauge length of 2.50") at a constant crosshead speed of 3"/min. (7.62 cm/min) with no hold.
(3) Strain the sample to Strains at a constant crosshead speed of 20"/min. (50.8 cm/min) with no hold.
(4) Reduce strain to 60% strain at a constant crosshead speed of 3"/min. (7.62 cm/min)
(5) Hold the sample at 60% strain for 5 minutes.
(6) Go to 0% strain at a constant crosshead speed 3"/min. (7.62 cm/min)

The reported unload force is the measured unload force of the stretch laminate (SL) at 60% strain after the 5 minute hold in step 5, normalized to Newton per 1 meter width of SL*basis weight of elastomer+adhesive (E+A) in the SL, N/(m·gsm)=N/(g/m), as shown in the equation below. The basis weight of the elastic and adhesive in the SL is calculated by dividing the grams of elastomer+adhesive in the SL by the area of the SL fully extended. The area of the fully extended stretch laminate ($A_{FESL}$) is defined as the area of the substrate of the stretch laminate in the absence of elastic and adhesive. The normalized unload force in $$N/(m \cdot gsm) = N/(g/m)$$

$$= \frac{\text{measured unload force (N)}}{[\text{width of } SL \text{ in meters} * ((\text{grams of } E + A) \div A_{FESL} \text{ in m}^2)]}.$$

For different sample dimensions, the crosshead speed is adjusted to maintain the appropriate strain rate for each portion of the test. For example, a crosshead speed of 10"/min (25.4 cm/min) would be used in Steps 1 and 3 for a sample gauge length of 1.25" (31.7 mm).

EXAMPLES

Film Preparation—Select stretch laminates are prepared using films comprising varying amounts of elastomeric polymer, modifying resin and mineral oil as shown in Table 1. The blending is accomplished by extrusion of the elastomer (Sample Film 1) or by solvent casting the mixture and pressing into a film on a heated Carver Press (Sample Films 2, 3, 4). The amount of each component is expressed in weight percent of the elastomeric composition. The examples in Table 1 comprise a styrene-isoprene-styrene (S-I-S) triblock copolymer, commercially available under the trade designation Vector® 4211 from Dexco Polymers L.P., Houston, Tex. In Sample Films 2-4, the elastomeric composition include white mineral oil, commercially available under the trade designation Bristol® 50T from Crompton Corporation, Petrolia, Pa. Sample Film 2 includes a modifying resin in the form of an alicyclic hydrocarbon resin under the trade designation Arkon P140, available from Arakawa Chemical Inc., Chicago, Ill. Sample Films 3 and 4 include a modifying resin in the form of poly(t-butyl styrene), synthesized at The Procter & Gamble Company via free radical polymerization of t-butylstyrene monomer available from Aldrich Chemical Company. The weight average molecular weight of the poly (t-butylstyrene) sample is 19 kDa as determined by gel permeation chromatography using polystyrene standards in tetrahydrofuran.

TABLE 1

| Elastomeric Composition (Weight %) | | | | |
|---|---|---|---|---|
| | Sample Film No. | | | |
| | 1* | 2 | 3 | 4 |
| Vector 4211 (SIS, 29% S) | 100 | 49 | 59 | 45 |
| Poly(t-butyl styrene), 19 kDa | | | 39 | 45 |
| Arkon P140 | | 49 | | |
| Mineral Oil, White Britol-50T | | 2 | 2 | 10 |

*Sample 1 is a comparative example whereas Samples 2-4 are embodiments of the present invention.

Laminate Preparation (Examples 1A, 2A-C, 3A-C, and 4A)—Stretch laminates numbered 1A, 2A, 2B, 2C, 3A, 3B, 3C, and 4A are prepared with the films disclosed in Table 1. The elastomeric films are resized to be approximately 2 cm wide by approximately 8 cm long. The mass of each elastomeric film is measured to the nearest 0.1 mg. The basis weight (grams per square meter, "gsm") of each film is calculated by dividing the film weight (in grams) by the film area (length by width in square meters). The stretch laminates in Table 2 are adhesively bonded multilayer laminate structures of a first nonwoven, the elastomeric film and a second nonwoven. The first nonwoven, available as supplier code 040018007 from Amoco Fabrics, Gronau, Germany, is a carded polypropylene thermally bonded nonwoven with a basis weight of 18 gsm. The second nonwoven, available from Sandler AG, Saale, Germany, under the supplier name Soft Sandler Topsheet VP 30/01/11, is a carded polypropylene, P11 thermally bonded nonwoven with a basis weight of approximately 30 gsm. The first nonwoven is bonded to the first surface of the elastomeric film using a single layer of adhesive applied in a spiral pattern in an amount of 18.6 gsm. The second nonwoven is bonded to the second surface of the elastomeric film using a single layer of adhesive applied in a spiral pattern in an amount of 18.6 gsm. A suitable adhesive is Findley 2861 available from Bostik, Inc., Middletown, Mass.

The stretch laminate preparation, stretching elastics to 400% strain, involves the following steps:
(1) Measure the width, length, thickness and weight of the elastomer film to be used in the stretch laminate. Attach a tape to each end of the film so the length of film between the tapes is 5 cm.
(2) Place the first nonwoven (2.54 cm wide×30 cm long) on a board and tape each end down to hold the laminate flat onto the board. The initial length of the nonwoven (Linw) between the tapes is 25 mm long.
(3) Place a glue strip (i.e., 18.6 gsm of the adhesive applied in a spiral pattern to one face of a 2.25 cm×28 cm sheet of release paper) centered on top of the nonwoven. Apply pressure to bond the adhesive to the nonwoven using an HR-100 roller (ASTM, 2 kg with 80 shore rubber) with 2 full strokes. Remove the release paper.
(4) Stretch the elastomeric film (2 cm wide non-stretched×5 cm long between tapes) to the initial length of the nonwoven between tapes (25 cm) and place it centered on top of the glue/nonwoven. The slow recovery elastic is stretched to 400% strain (5 cm to 25 cm).
(5) Place a glue strip, which similar to the one described in step (3), centered on top of the stretched elastomeric film. Apply pressure to bond (HR-100, 2 full strokes) and remove the release paper). The two strips of glue spirals used in steps 3 and 5 add approximately 0.21 grams of adhesive to the stretch laminate. The area of the fully extended slow recovery stretch laminate ($A_{FESL}$) is 0.00635 m² (25 cm long by 2.54 cm wide between tapes).
(6) Place the second nonwoven (2.54 cm wide×25 cm long between tapes) centered on top of the laminate. Apply pressure with the roller (HR-100, 10 full strokes) to bond the laminate.
(7) Remove the laminate structure from the board and let rest overnight at room temperature or 30 minutes at 37° C. Measure the final length of the gathered laminate between the tapes without stretching. Calculate the maximum percent strain (Max % Strain) available to the laminate during elongation without exceeding the original length of the nonwoven using the equation:

$$\text{Max \% Strain} = 100 * ((Linw - L_g)/L_g)$$

where $L_g$ is the gathered length of stretch laminate and Linw is the initial length of nonwoven. Stretch laminates 1A, 2A, 3A and 4A in Table 2 are prepared with films of the elastomeric compositions (Table 1) stretched to 400% strain; these stretch laminates have maximum percent strains ≧200%. The elastomer film properties (for example basis weight and modulus) and the percent strain of the elastomer film during stretch laminate preparation will influence the degree of gathering in the finished laminate. Stretch laminates 2B, 2C, 3B and 3C in Table 2 are prepared with films of the elastomeric compositions (Table 1) stretched to 240% strain (2B, 3B) or 200% strain (2C, 3C). The maximum percent strain for these stretch laminates and the initial percent strain used in the Post Elongation Recovery Test are shown in Table 2.

TABLE 2

Stretch Laminate Samples Prepared with Elastomeric Films in Table 1

| Example | Sample Film # | % Strain of Elastic During Laminate Preparation (%) | Maximum % Strain of Laminate (%) | Initial % Strain of Laminate in Post Elongation Recovery Test (%) |
|---|---|---|---|---|
| 1A | 1 | 400 | 335 | 199 |
| 2A | 2 | 400 | 238 | 199 |
| 2B | 2 | 240 | 149 | 148 |
| 2C | 2 | 200 | 137 | 100 |
| 3A | 3 | 400 | 233 | 200 |
| 3B | 3 | 240 | 155 | 148 |
| 3C | 3 | 200 | 135 | 100 |
| 4A | 4 | 400 | 210 | 200 |

Stretch Laminate Preparation (Comparative Examples 6-12)—Comparative Examples 6-12 are stretch laminates from commercially available diapers. The stretch laminates are removed from the diaper in the relaxed, unstretched state (leg cuff, side panel, or waist). Stretch laminates samples from the waist and side panels are cut into specimen approximately 6.4 mm wide by approximately 20 mm long, where the length is the same direction as the laminate is stretched during diaper use. The center two inches of the gathered elastic waist laminate was separated from the Huggies Supreme Baby Shaped diapers. The outer cover (laminate of nonwoven, polymer film and nonwoven) was removed from the waist feature. Samples of the resulting stretch laminate were cut with dimensions of approximately 6.4 mm wide by approximately 20 mm long, where the length is in the same direction as the laminate is stretched during diaper use. The leg cuffs are removed from the diapers and the ends are trimmed off. The resulting stretch laminate is cut into specimen approximately 20 mm long and trimmed to approximately 6.4 mm wide maintaining all of the elastics members of the leg cuff, which may not be centered in the width. The initial percent strain (200%±5%, 150%±5%, 100%±5%) used in the Post Elongation Recovery Test to test each comparative example is shown in

TABLE 3

Comparative Examples of Stretch Laminate from Diapers

| Laminate Sample | Description | Initial % Strain of Laminate in Post Elongation Recovery Test (%) |
|---|---|---|
| 6 | Huggies Pull-Ups Side Panel | 199 |
| 7 | Pampers Cruisers Stretch Ear | 199 |
| 8 | Huggies Outer Leg Cuff | 148 |
| 9 | Huggies Inner Leg Cuff | 149 |
| 10 | Pampers Cruisers Inner Leg Cuff | 146 |
| 11 | Huggies Supreme Waistband | 100 |
| 12 | Pampers Cruisers Outer Leg Cuff | 99 |

Stretch laminate samples from Tables 3, which include stretch laminates of current diaper products (samples 6, 7, 8, 9, 10, 11, and 12) are measured according to the Post Elongation Recovery method described in the Test Methods section above. The results are shown in Table 4 (Initial Strain of approximately 200%), Table 5 (Initial Strain of approximately 150%) and Table 6 (Initial Strain of approximately 100%). The basis weight of the elastomeric films from Table 1 used to prepare the stretch laminate samples tested (2A, 2B, 2C, 3A, 3B, 3C, 4A) are reported. The force measured (not normalized for film mass, or thickness) in Newtons to strain the laminate sample to the Initial % Strain are reported. The percent of initial strain remaining is reported at different recovery times (15 seconds, 30 seconds, 60 seconds, and 3 minutes), where the percent of initial strain remaining is calculated with the equation:

Percent of initial strain remaining=100×[% Strain at time (t)/Initial % Strain]

For the samples reported in Table 6 (Initial Strain of approximately 100%), the percent strains are also reported for each of the recovery times.

TABLE 4

Percent of Initial Strain of Stretch Laminates Remaining After Stretch to 200% Initial Strain

| | Laminate Sample | | | | | |
|---|---|---|---|---|---|---|
| | 1A | 2A | 3A | 4A | 6 | 7 |
| Percent of Initial Strain Remaining at 22° C. (72° F.) | | | | | | |
| Film basis weight (gsm) | 127 | 148 | 142 | 112 | — | — |
| Force (N) to initial strain | 4.1 | 1.9 | 1.8 | 2.0 | 0.7 | 1.1 |
| % of initial strain after 15 seconds recovery | 4 | 22 | 22 | 37 | 4 | 5 |
| % of initial strain after 30 seconds recovery | 3 | 15 | 15 | 27 | 4 | 5 |
| % of initial strain after 60 seconds recovery | 3 | 10 | 10 | 19 | 3 | 5 |
| % of initial strain after 3 minutes recovery | 3 | 6 | 5 | 10 | 3 | 4 |
| Percent of Initial Strain Remaining at 32° C. (90° F.) | | | | | | |
| Film basis weight (gsm) | 124 | 148 | 142 | 121 | — | — |
| Force (N) to initial strain | 3.4 | 1.3 | 1.3 | 1.3 | 0.7 | 1.1 |
| % of initial strain after 15 seconds recovery | 3 | 9 | 10 | 20 | 4 | 6 |
| % of initial strain after 30 seconds recovery | 3 | 6 | 7 | 13 | 3 | 6 |
| % of initial strain after 60 seconds recovery | 2 | 5 | 5 | 8 | 3 | 5 |
| % of initial strain after 3 minutes recovery | 2 | 3 | 4 | 5 | 3 | 5 |

TABLE 5

Percent of Initial Strain of Stretch Laminates Remaining After Stretch to 150% Initial Strain

| Percent of Initial Strain Remaining at 22° C. | Laminate Sample | | | | |
|---|---|---|---|---|---|
| (72° F.) | 2B | 3B | 8 | 9 | 10 |
| Film basis weight (gsm) | 126 | 155 | — | — | — |
| Force (N) to initial strain | 2.1 | 1.9 | 4.0 | 2.7 | 1.7 |
| % of initial strain after 15 seconds recovery | 34 | 30 | 6 | 6 | 6 |
| % of initial strain after 30 seconds recovery | 24 | 21 | 5 | 5 | 5 |
| % of initial strain after 60 seconds recovery | 16 | 14 | 4 | 5 | 5 |
| % of initial strain after 3 minutes recovery | 9 | 8 | 3 | 4 | 4 |

TABLE 5-continued

Percent of Initial Strain of Stretch Laminates Remaining After Stretch to 150% Initial Strain

| Percent of Initial Strain Remaining at 22° C. | Laminate Sample | | | | |
|---|---|---|---|---|---|
| (72° F.) | 2B | 3B | 8 | 9 | 10 |

TABLE 6

Percent of Initial Strain of Stretch Laminates Remaining After Stretch to 100% Initial Strain

| Percent of Initial Strain Remaining at 22° C. | Laminate Sample | | | |
|---|---|---|---|---|
| (72° F.) | 2C | 3C | 11 | 12 |
| Film basis weight (gsm) | 132 | 163 | — | — |
| Force (N) to initial strain | 1.3 | 1.5 | 0.6 | 0.7 |
| Initial % Strain | 100 | 100 | 100 | 99 |
| % of initial strain after 15 seconds recovery | 43 | 30 | 8 | 7 |
| % strain after 15 seconds of recovery | 42 | 30 | 8 | 7 |
| % of initial strain after 30 seconds recovery | 32 | 21 | 7 | 6 |
| % strain after 30 seconds of recovery | 32 | 21 | 7 | 6 |
| % of initial strain after 60 seconds recovery | 23 | 14 | 7 | 5 |
| % strain after 60 seconds of recovery | 23 | 14 | 7 | 5 |
| % of initial strain after 3 minutes recovery | 13 | 8 | 6 | 4 |
| % strain after 3 minutes of recovery | 13 | 8 | 6 | 4 |

The unload forces of stretch laminates in Table 2 (1A, 2A, 3A and 4A), prepared with films of the elastomeric compositions strained to 400%, are measured at 21° C. and 37° C. according to the 2-Cycle Hysteresis Test described in the Test Methods Section above. The whole stretch laminate is placed in the grips, centered by width and length, during the 2 Cycle Hysteresis test. The results are shown in Table 8.

TABLE 7

Unload Forces N/(g/m) of Laminates

| | Sample | | | |
|---|---|---|---|---|
| | 2A | 3A | 4A | 5** |
| Normalized Unload Force at 21° C. (70° F.) [N/(meter width laminate · gsm E + A)] | 0.31 | 0.26 | 0.20 | 0.11 |
| Normalized Unload Force at 37° C. (99° F.) [N/(meter width laminate · gsm E + A)] | 0.29 | 0.25 | 0.19 | 0.10 |

**Sample No. 5 is a comparative example of a laminate made with film of Findley H2401 adhesive (pressed into a film using a heated Carver Press).

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with a definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a) a topsheet;
   b) a backsheet joined with the topsheet;
   c) an absorbent core interposed between the topsheet and backsheet; and
   d) an article element selected from the group consisting of an anal cuff, an elasticized topsheet, a fastening system, a leg cuff, a waist elastic feature, a side panel, an ear, and combinations thereof;
   wherein said article element comprises a slow recovery stretch laminate exhibiting an unload force at 37° C. of about 0.16 N/(g/m) or greater and a percent of initial strain after 15 seconds of recovery at 22° C. of 10% or greater.

2. The absorbent article of claim 1 wherein the slow recovery stretch laminate exhibits a percent of initial strain after 15 seconds of recovery at 22° C. of about 20% or greater.

3. The absorbent article of claim 1 wherein the slow recovery stretch laminate exhibits a percent of initial strain after 15 seconds of recovery at 22° C. of about 30% or greater.

4. The absorbent article of claim 1 wherein the slow recovery stretch laminate exhibits a percent of initial strain after 15 seconds of recovery at 32° C., wherein the difference of the percent of initial strain after 15 seconds of recovery at 22° C. and the percent of initial strain after 15 second of recovery at 32° C. is greater than or equal to about 5%.

5. The absorbent article of claim 1 wherein the slow recovery stretch laminate comprises
   a) at least a first substrate having a first surface and a second surface
   b) at least one elastic member joined to the first surface of the substrate.

6. The absorbent article of claim 5 wherein the slow recovery stretch laminate further comprises a second substrate having a first surface and a second surface, wherein the elastic member is joined to the first surface of the second substrate such that the elastic member is disposed between the first substrate and the second substrate.

7. The absorbent article of claim 5 wherein the elastic member is joined to the first surface of the substrate with an adhesive.

8. The absorbent article of claim 5 wherein the elastic member comprises
   a) about 20% to about 100% of at least one elastomeric polymer,
   b) optionally, about 0.01% to about 60% of at least one modifying resin; and
   c) optionally, about 0.01% to about 60% of at least one additive.

9. The absorbent article of claim 7 wherein the elastomeric polymer is selected from the group consisting of styrenic block copolymers, natural and synthetic rubbers, polyisoprene, neoprene, polyurethanes, silicone rubbers, hydrocarbon elastomers, ionomers, and combinations thereof.

10. The absorbent article of claim 7 wherein the elastomeric polymer is a block copolymer comprising at least one substantially soft block and at least one substantially hard block.

11. The absorbent article of claim 7 wherein the modifying resin is selected from the group consisting of unhydrogenated C5 hydrocarbon resins or C9 hydrocarbon resins, partially and fully hydrogenated C5 hydrocarbon resins or C9 hydrocarbon resins; cycloaliphatic resins; terpene resins; polystyrene and styrene oligomers; poly(t-butylstyrene) or oligomers thereof; rosin and rosin derivatives; coumarone indenes; polycyclopentadiene and oligomers thereof; polymethylstyrene or oligomers thereof; phenolic resins; indene polymers, oligomers and copolymers; acrylate and methacrylate oligomers, polymers, or copolymers; derivatives thereof; and combinations thereof.

12. The absorbent article of claim 7 wherein the slow recovery stretch laminate further comprises an additive selected from the group comprising stabilizers, antioxidants, viscosity modifiers, processing aids, bacteriostats, colorants, fillers, or combinations thereof.

13. The absorbent article of claim 5 wherein the elastic member is in a form selected from the group consisting of a film, a strand, a band, a cross-hatch array, a foam, and combinations thereof.

14. The absorbent article of claim 5 wherein the first substrate is selected from the group consisting of nonwoven webs, woven webs, knitted fabrics, films, film laminates, apertured films, nonwoven laminates, sponges, foams, scrims, and combinations thereof.

15. The absorbent article of claim 1 wherein the absorbent article is selected from the group comprising diapers, training pants, pull-on garments, refastenable pants, adult incontinence products, or feminine care products.

16. The absorbent article of claim 10 wherein the elastomeric polymer is a triblock copolymer comprising a hard/soft/hard block configuration.

17. The absorbent article of claim 10 wherein the elastomeric polymer is a triblock copolymer selected from the group comprising styrene/isoprene/styrene.

18. The absorbent article of claim 1 wherein the elasticized topsheet further comprises a slit opening allowing for waste passage.

19. The absorbent article of claim 1 wherein the slow recovery stretched laminate is joined to the elasticized topsheet and runs substantially longitudinally adjacent to the slit opening.

20. The absorbent article of claim 8 wherein the modifying resin has a glass transition temperature of about 60° C. to about 180° C.

21. The absorbent article of claim 8 wherein the modifying resin has a glass transition temperature of about 70° C. to about 150° C.

22. The absorbent article of claim 8 wherein the modifying resin has a glass transition temperature of about 90° C. to about 130° C.

23. The absorbent article of claim 1 wherein the slow recovery stretch laminate exhibits a percent of initial strain after 15 seconds of recovery at 22° C. of about 40% or greater.

24. The absorbent article of claim 1 wherein the slow recovery stretch laminate comprises a slow recovery elastomer that exhibits a normalized unload force at 37° C. of greater than about 0.04 N/mm$^2$.

25. The absorbent article of claim 24 wherein the slow recovery elastomer exhibits a post elongation strain of at least about 50% after 15 seconds of recovery at 22° C.

* * * * *

UNITED STATES PATENT AND TRADEMARK OFFICE
CERTIFICATE OF CORRECTION

PATENT NO. : 7,905,872 B2  Page 1 of 1
APPLICATION NO. : 11/144497
DATED : March 15, 2011
INVENTOR(S) : McKiernan et al.

It is certified that error appears in the above-identified patent and that said Letters Patent is hereby corrected as shown below:

Column 23
Line 52, delete "Strains" and insert --$Strain_i$--.

Signed and Sealed this
Twenty-first Day of June, 2011

David J. Kappos
*Director of the United States Patent and Trademark Office*